United States Patent
Radomsky et al.

(10) Patent No.: US 9,078,910 B2
(45) Date of Patent: Jul. 14, 2015

(54) COMPOSITIONS COMPRISING SPICAMYCIN DERIVATIVES AND METHODS OF USE THEREOF

(71) Applicant: DARA BioSciences, Inc., Raleigh, NC (US)

(72) Inventors: Michael Radomsky, Chagrin Falls, OH (US); Mary Katherine Delmedico, Raleigh, NC (US); Linda Jett, Hillsborough, NC (US)

(73) Assignee: DARA BIOSCIENCES, INC., Raleigh, NC (US)

( * ) Notice: Subject to any disclaimer, the term of this patent is extended or adjusted under 35 U.S.C. 154(b) by 0 days.

(21) Appl. No.: 13/962,279

(22) Filed: Aug. 8, 2013

(65) Prior Publication Data

US 2014/0045780 A1 Feb. 13, 2014

Related U.S. Application Data

(60) Provisional application No. 61/681,385, filed on Aug. 9, 2012, provisional application No. 61/730,311, filed on Nov. 27, 2012, provisional application No. 61/736,138, filed on Dec. 12, 2012.

(51) Int. Cl.
| | | |
|---|---|---|
| *A01N 43/04* | (2006.01) |
| *A61K 31/70* | (2006.01) |
| *A61K 31/7076* | (2006.01) |
| *A61K 9/00* | (2006.01) |
| *A61K 45/06* | (2006.01) |
| *A61K 47/10* | (2006.01) |

(52) U.S. Cl.
CPC .......... *A61K 31/7076* (2013.01); *A61K 9/0019* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | |
|---|---|---|
| 5,461,036 A | 10/1995 | Otake et al. |
| 5,631,238 A | 5/1997 | Otake et al. |
| 5,905,069 A * | 5/1999 | Borsook et al. ................. 514/45 |
| 7,196,071 B2 | 3/2007 | Borsook |
| 7,375,094 B2 | 5/2008 | Borsook |
| 7,632,825 B2 | 12/2009 | Borsook |
| 2011/0237536 A1* | 9/2011 | Didsbury et al. .............. 514/45 |

FOREIGN PATENT DOCUMENTS

EP 0525479 A1 2/1993

OTHER PUBLICATIONS

Overbeck et al. Circ Res. (1970), vol. 26, pp. 717-731.*
U.S. Appl. No. 13/122,771, Sep. 29, 2011, Didsbury et al.
Abdi S et al: "The Effects of KRN5500, a Spicamycin Derivative, on Neuropathic and Nociceptive Pain Models in Rats," Jan. 1, 2000, pp. 955-959, vol. 91, No. 4., Williams and Wilkins, Baltimore MD, US.
Borsook D et al: "Antineuropathic Effects of the Antibiotic Derivative Spicamycin KRN5500," Pain Medicine, Mar. 1, 2004, pp. 104-108, vol. 5, No. 1, Blackwell Science, Malden, US.
DiLorenzo L et al: "A Water-Soluble Synthetic Spicamycin Derivative (San-Gly) Decreases Mechanical Allodynia in a Rodent Model of Neuropathic Pain," Neuroscience Letters, Sep. 13, 2002, pp. 37-40, vol. 330 No. 1, Limerick, IE.
Yamamoto et al: "Phase 1 and Pharmacokinetic Study of KRN5500, a Spicamycin Derivative, for Patients with Advanced Solid Tumors," Jpn J Clin Oncol, 2003, pp. 302-308, vol. 33, No. 6, Foundation for Promotion of Cancer Research, JP.

* cited by examiner

*Primary Examiner* — Patrick Lewis
(74) *Attorney, Agent, or Firm* — Alston & Bird LLP

(57) ABSTRACT

The present invention relates to compositions comprising spicamycin derivatives, methods of making such compositions, and their use in the treatment and/or prevention of pain, including neuropathic pain.

39 Claims, 2 Drawing Sheets

COMPOSITIONS COMPRISING SPICAMYCIN DERIVATIVES AND METHODS OF USE THEREOF

CROSS-REFERENCE TO RELATED APPLICATIONS

This application claims the benefit of U.S. Provisional Application No. 61/681,385, filed Aug. 9, 2012, U.S. Provisional Application No. 61/730,311, filed Nov. 27, 2012, and U.S. Provisional Application No. 61/736,138, filed Dec. 12, 2012, the contents of which are herein incorporated by reference in their entirety.

FIELD OF THE INVENTION

The present invention relates to compositions comprising spicamycin derivatives, methods of making such compositions, and their uses.

BACKGROUND OF THE INVENTION

Neuropathic pain is a chronic pain that results from nerve damage, is characterized by an abnormal hypersensitivity to innocuous as well as noxious stimuli, and often persists after the tissue damage and inflammation that initially caused the pain have healed. Eleven million patients worldwide are afflicted by neuropathic pain (Olsen, *WWMR, Inc. Consulting and Marketing Report* (2002)). Clinically, neuropathic pain is difficult to manage, fails to respond to standard analgesic treatments, and often worsens over time (Amer et al., *Acta Anaesthesiol. Scand.* 29:32 (1985); Chemy et al., *Neurology* 44:857 (1994)).

The present invention provides improved compositions and methods for treating or preventing pain, including neuropathic pain, using spicamycin derivatives.

SUMMARY OF THE INVENTION

The present invention provides compositions comprising a spicamycin derivative formulated in combination with a first biocompatible organic solvent that solubilizes the spicamycin derivative, a second biocompatible organic solvent that is miscible with the first biocompatible organic solvent and solubilizes the spicamycin derivative, and a surfactant. The compositions of the invention are not plagued by the shortcomings of previous formulations. This is due to providing enhanced solubility of the spicamycin derivative, improving ease of manufacturing, preparation and administration, and reducing levels of undesirable excipients in the final preparations.

The present invention also provides methods for preparing a concentrated solution comprising a spicamycin derivative, methods for preparing an intravenous solution comprising a spicamycin derivative, and methods for treating or preventing pain or neurotoxicity in a subject, comprising administering to a subject in need thereof a prevention or treatment effect amount of the compositions of the invention that comprise a spicamycin derivative.

Accordingly, in one embodiment, the invention provides a composition comprising a spicamycin derivative of Formula II, wherein $R_1$ and $R_2$ are different from each other and represent H or OH, and R represents a substituted or unsubstituted alkyl, alkenyl, alkynyl, or cycloalkyl, or a pharmaceutically acceptable salt, prodrug, or optical isomer thereof. The composition further comprises a first biocompatible organic solvent that solubilizes the spicamycin derivative, a second biocompatible organic solvent that is miscible with the first biocompatible organic solvent and solubilizes the spicamycin derivative, and a surfactant. The composition of this embodiment is a spicamycin derivative dissolved in organic solvent to form a liquid that is substantially free of particulates and essentially free of mono-ethanolamine. The composition of this embodiment can further comprise an aqueous intravenous liquid or diluent.

In another embodiment, the invention provides a method for preparing a concentrated solution comprising a spicamycin derivative of the invention. The method comprises the steps of contacting a spicamycin derivative with a first biocompatible organic solvent that solubilizes the spicamycin derivative and a surfactant to form a first composition. The first composition is then contacted with a second biocompatible organic solvent that is miscible with the first biocompatible organic solvent to form a concentrated solution that is substantially free of particulates and is essentially free of mono-ethanolamine.

In another embodiment, the invention provides methods for preparing an intravenous solution comprising a spicamycin derivative of the invention. The method comprises the step of contacting the concentrated solution produced by the method above with an intravenous infusion liquid or diluent, wherein the resulting intravenous solution is substantially free of particulates.

In yet another embodiment, the invention provides methods for treating or preventing pain in a subject, comprising administering to a subject in need thereof a preventative or treatment effective amount of the compositions of the invention that comprise a spicamycin derivative. In one such embodiment, the pain is neuropathic pain. In additional embodiments, the composition of the invention can be used in methods for treating or preventing neurotoxicity in a subject.

The present invention is explained in greater detail in the drawings herein and in the specification set forth below.

DETAILED DESCRIPTION OF THE INVENTION

Figure 1:
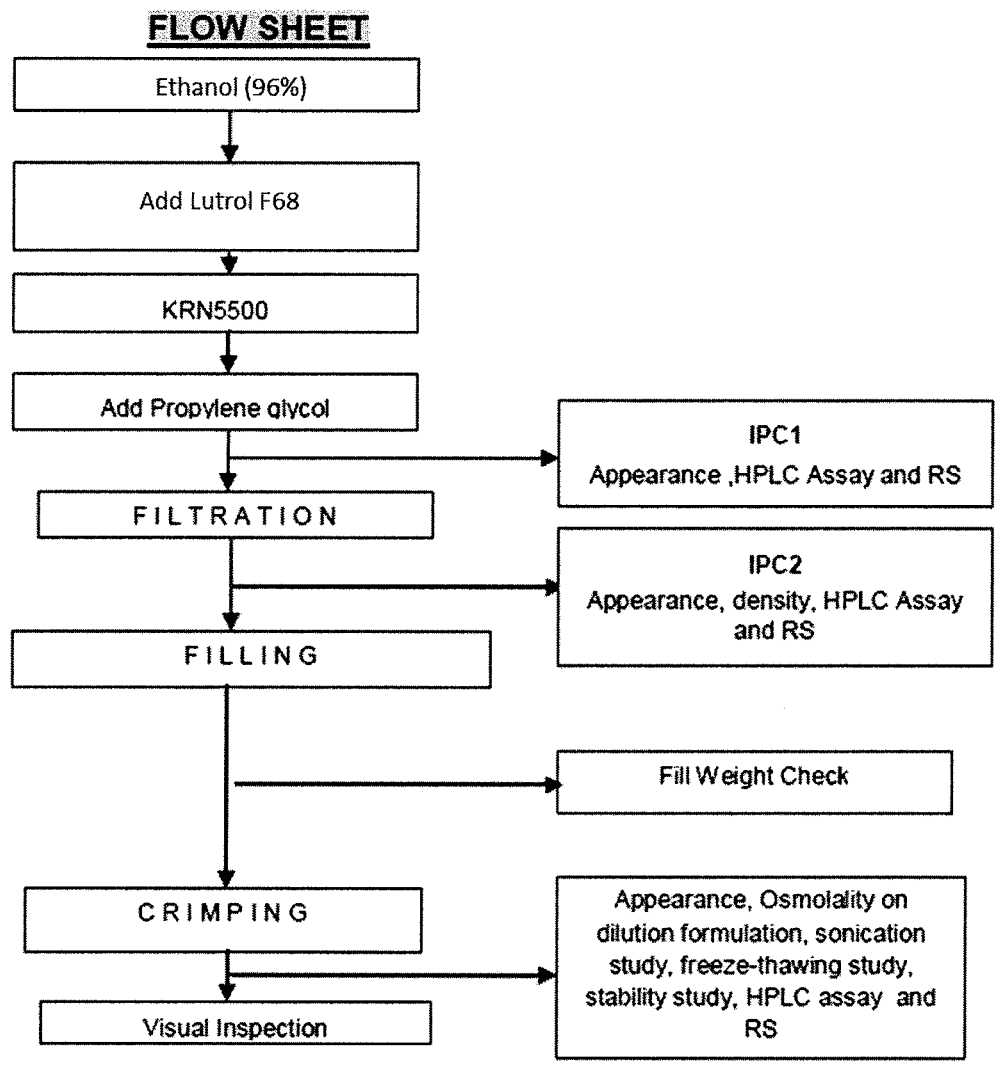
FIG. 1 shows a manufacturing process flow chart for the production of a composition of the invention, wherein the surfactant is Lutrol F68.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition.

The term "materially altered," as applied to a composition, refers to an increase or decrease in the therapeutic effectiveness of the composition of at least about 20% or more as compared to the effectiveness of a composition consisting of the recited components.

The term "treatment effective amount," "prevention effective amount," or "effective amount," as used herein, refers to that amount of a composition of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

"Prevent" or "preventing" or "prevention" refer to prevention or delay of the onset of the disorder and/or a decrease in the level of pain in a subject relative to the level of pain that would develop in the absence of the methods of the invention. The prevention can be complete, e.g., the total absence of pain in a subject. The prevention can also be partial, such that the occurrence of pain in a subject is less than that which would have occurred without the present invention.

Methods of assessing pain or pain relief are known in the art (e.g., subjective evaluation of pain by a patient), and standard animal models of pain are available such as the Randall Selitto or Bennet Xie rat models for pain; experimentally produced segmental spinal nerve injury or chronic constriction nerve injury (see, e.g., Kim et al., *Pain* 50:355 (1992); Bennett et al., *Pain* 33:87 (1988) and U.S. Patent Publication 2004/0038927); see also, Abdi et al., *Anesth. Analg.* 91:955 (2000). Models of neuropathic pain are also described in Zeltser et al., *Pain* 89:19 (2000); Seltzer et al., *Pain* 43:205 (1990); and Decosterd et al., *Pain* 87:149 (2000).

The term "neuropathic pain" is understood in the art and encompasses pain arising from injury to or pathological changes in the central nervous system and/or peripheral nervous system (reviewed in Woolf, *Acta Neurochir* 58:125 (1993)). Patients with neuropathic pain typically present with a characteristic set of sensory disorders independent of the cause, including a constant scalding or burning pain, a partial loss of sensitivity, tactile or cold allodynia and/or hyperpathia to repeated stimulation. Neuropathic pain arises from a number of diverse conditions, the most common of which are chemotherapy-induced pain, trigeminal neuralgia, postherpetic neuralgia, painful diabetic neuropathy, and the reflex sympathetic dystrophies including causalgia, mononeuropathies, and peripheral nerve injury. In general, neuropathic pain tends to be resistant to opioids and non-steroidal anti-inflammatories (NSAIDS), whereas nociceptive pain usually responds well to both of these treatment modalities. Few non-surgical alternatives exist for a patient with a disabling pain resistant to opioid drugs.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 20 ed. 2005). Exemplary pharmaceutically acceptable carriers for the compositions of this invention include, but are not limited to, sterile pyrogen-free water and sterile pyrogen-free physiological saline solution.

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. No. 6,680,324 and U.S. Pat. No. 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The term "alkyl" denotes a straight or branched hydrocarbon chain containing 1-24 carbon atoms, e.g., 1-12 carbon atoms. Examples of alkyl group include methyl, ethyl, propyl, isopropyl, butyl, isobutyl, tert-butyl, and the like.

The term "alkenyl" denotes a straight or branched hydrocarbon chain containing 1-24 carbon atoms, e.g., 1-12 carbon atoms, and containing one or more double bonds, e.g., 1, 2, 3, or 4 double bonds.

The term "alkynyl" denotes a straight or branched hydrocarbon chain containing 1-24 carbon atoms, e.g., 1-12 carbon atoms, and containing one or more triple bonds, e.g., 1, 2, 3, or 4 triple bonds.

The term cycloalkyl refers to non-aromatic cyclic hydrocarbon moieties containing 3-24 carbon atoms, e.g., 3-12 carbon atoms. The cycloalkyl group can contain one or more double bonds. Examples include cyclopropyl, cyclobutyl, cyclopentyl, and cyclohexyl.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The terms "halo" and "halogen" refer to any radical of fluorine, chlorine, bromine or iodine.

The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to an aromatic 5-8 membered monocyclic, 8-12 membered bicyclic, or 11-14 membered tricyclic ring system wherein 0, 1, 2, or 3 atoms of each ring can be substituted by a substituent. Examples of aryl groups include phenyl, naphthyl and the like.

The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heterocyclyl groups include piperizinyl, pyrrolidinyl, dioxanyl, morpholinyl, tetrahydrofuranyl, and the like.

Suitable substituents for aryl, heteroaryl, and heterocyclyl groups are the same as the substituents for alkyl groups.

The terms "solubilizes" and "soluble" refer to the ability of a solid or liquid substance to dissolve into a liquid solvent to form a homogeneous solution.

The term "biocompatible" refers to organic solvents that do not induce toxic or unwanted side effects when administered to a patient in certain amounts.

The term "miscible" refers to the ability of a liquid to mix evenly into another liquid.

The present invention provides compositions comprising a spicamycin derivative of Formula II in combination with additional constituents, including a first biocompatible organic solvent that solubilizes the spicamycin derivative, a second biocompatible organic solvent that is miscible with the first biocompatible organic solvent and solubilizes the spicamycin derivative, and a surfactant, wherein the spicamycin derivative can be a pharmaceutically acceptable salt, prodrug, or optical isomer thereof. The composition of this embodiment forms a liquid that is substantially free of particulates and is essentially free of mono-ethanolamine. The terms "first" and "second" as used herein are only meant to differentiate between the biocompatible organic solvents of the invention. These terms do not indicate or suggest any order in which the biocompatible organic solvents should be contacted with the spicamycin derivative or the surfactant.

In some embodiments, the first biocompatible organic solvent is selected from the group consisting of ethanol and t-butanol, and other biocompatible alcohols. In a particular embodiment, the first biocompatible organic solvent is ethanol, having a purity of at least about 96% (v/v). The first biocompatible organic solvent is preferably a pharmaceutical grade excipient that increases the solubility of the composition components and adjusts the physical properties (i.e. viscosity) of the composition to improve manufacturability. The first biocompatible organic solvent can be particularly capable of enhancing the solubility of the surfactant of the composition and the spicamycin derivative of the composition. The first biocompatible organic solvent can also be capable of enhancing the solubility of any additional excipients added to the composition.

In some embodiments, the second biocompatible organic solvent is selected from the group consisting of propylene glycol, glycerin, polyethylene glycol, and polypropylene glycol. In a particular embodiment, the second biocompatible organic solvent is propylene glycol. The second biocompatible organic solvent is preferably a pharmaceutical grade excipient that advantageously enhances the solubility of the spicamycin derivatives described herein when compared to aqueous or ethanol-only formulations. The second biocompatible organic solvent can also be capable of enhancing the solubility of any additional excipients added to the composition.

A surfactant is included in the composition of the invention to improve the solubility of the spicamycin derivative when a concentrated solution of the composition is diluted into an aqueous intravenous liquid or diluent (e.g., 5% dextrose, 0.9% sodium chloride, or Lactated Ringers solution). In some embodiments, the surfactant is a pharmaceutical grade excipient selected from the group consisting of polysorbate, poloxamer (e.g., Lutrol), n-dodecyl-b-maltoside, tocopheryl-polyethylene glycol succinate, polyethylene glycol, a polyoxyl, Solutol, Pluronics, sodium dodecyl sulfate, SPAN, and octoxynol-9. In a particular embodiment, the surfactant is polysorbate.

Although compositions comprising a spicamycin derivative can be prepared in combination with the first biocompatible organic solvent and the second biocompatible solvent above as a clear, colorless solution in the absence of a surfactant, some precipitation may be observed when diluted into an aqueous intravenous liquid or diluent.

The composition of the invention is advantageous because it does not require the use of certain solvents. Formulations that contain certain organic solvents can potentially induce unwanted or untold side effects. Additionally, a multi-step procedure to prepare a dosing solution in an intravenous liquid or diluent from a vial and ampoule, is not required for the present compositions. These compositions can be prepared for administration, wherein a concentrated solution can be withdrawn from a vial with a syringe and diluted and mixed into an aqueous intravenous liquid or diluent (e.g., 5% dextrose, 0.9% sodium chloride, Lactated Ringers solution). The composition of the invention can also be manufactured with standardized excipients and equipment, wherein no special homogenization or other equipment is required. Additionally, while it is advantageous that the excipients utilized in the composition of the invention are known, it is the combination of excipients disclosed herein that provide a superior formulation.

The spicamycin derivatives included in the composition of the invention also exhibit enhanced solubility in both a concentrated solution and when diluted into an aqueous intravenous liquid or diluent. Furthermore, the composition of the invention can comprise spicamycin derivatives at higher concentrations than formulations previously disclosed in the art, which allows for lower infusion volumes and shorter times of administration. Moreover, the levels of excipients in the composition of the invention are within established limits for pharmaceutical products.

Spicamycin is an anti-tumor antibiotic produced by the bacterium *Streptomyces alansinicus* 879-MT$_3$ (Hayakawa et al. *Agric. Biol. Chem.* 49:2685 (1985)). The naturally occurring compound has the following general structure of Formula I, varying solely in the fatty acid moiety.

Formula 1

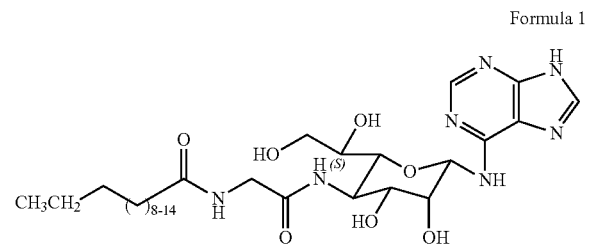

Synthetic spicamycin derivatives and their use as anti-tumor agents are described in U.S. Pat. Nos. 5,461,036 and 5,631,238 to Otake et al. The use of spicamycin or derivatives thereof, including KRN5500, to reduce and/or prevent pain is described in U.S. Pat. Nos. 5,905,069, 7,196,071, and 7,375,094 to Borsook et al. and in U.S. application Ser. No. 13/122,771 to Didsbury et al. KRN5500 has been demonstrated to be effective in rat models of neuropathic pain (Abdi et al., *Anesth. Analg.* 91:955 (2000); Kobierski et al., *Anesth. Analg.* 97:174 2003). However, suitable formulations of spicamycin and its derivatives for injection are lacking.

Accordingly, in one embodiment, the invention provides a composition comprising a compound of Formula II, wherein $R_1$ and $R_2$ are different from each other and represent H or OH, and R represents a substituted or unsubstituted alkyl, alkenyl, alkynyl, or cycloalkyl, or a pharmaceutically acceptable salt, prodrug, or optical isomer thereof. Formula II has the following structure:

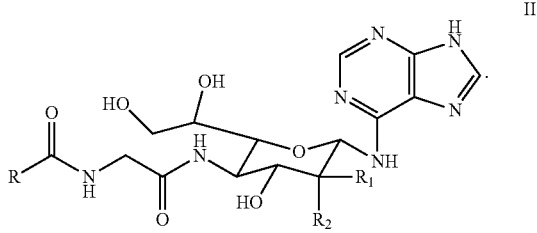

II

The spicamycin derivative of the invention can be a pharmaceutically acceptable salt, prodrug, or optical isomer thereof, and is dissolved in organic solvent to form a liquid that is substantially particulate free and is essentially free of monoethanolamine (ethanolamine).

This embodiment of the composition further comprises a first biocompatible organic solvent that solubilizes the spicamycin derivative, a second biocompatible organic solvent that is miscible with the first biocompatible organic solvent and solubilizes the spicamycin derivative, and a surfactant. This embodiment of the composition can also be substantially free or essentially free of additional excipients that alter an advantageous property of the formulation, such as mono-ethanolamine or N,N-dimethylacetamide (DMAC). Preferred amounts of each component present in the composition of the invention are disclosed elsewhere herein.

In another embodiment, the spicamycin derivative in the composition of the invention comprises the compound of Formula II where R is selected from the group consisting of a linear alkenyl having 11-13 carbon atoms; a linear, unsubstituted alkyl having 11-13 carbon atoms and no double or triple bonds; a linear haloalkyl having 10-15 carbon atoms; $CH_3(CH_2)_nCH(OH)$— or $CH_3(CH_2)_{n-1}CH(OH)CH_2$—, wherein n denotes an integer from 9-13; an alkyl having 10-15 carbon atoms substituted with an azide group or a cyano group; a linear alkyl having 10-13 carbon atoms substituted with a phenoxy group or a halogen-substituted phenoxy group;

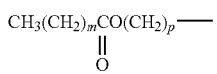

wherein m denotes an integer from 0-2 and p denotes an integer from 9-14;

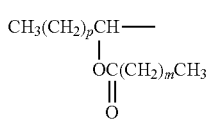

wherein m denotes an integer from 0-2 and p denotes an integer from 8-13;

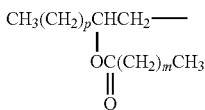

wherein m denotes an integer from 0-2 and p denotes an integer from 10-15; $CH_3(CH_2)_mSO_2O(CH_2)_p-$, wherein m denotes an integer from 0-3 and p denotes an integer from 9-14;

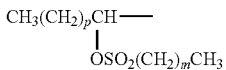

wherein m denotes an integer from 0-3 and p denotes an integer from 10-15;

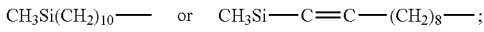
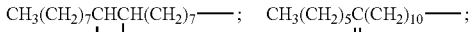
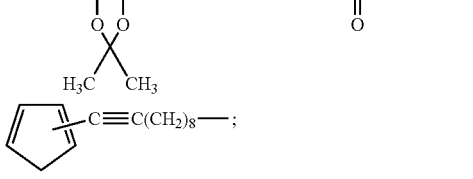

and a linear alkadienyl having 11-13 carbon atoms.

In another embodiment, R is selected from a linear alkenyl having 11-13 carbon atoms; a linear, unsubstituted alkyl having 11-13 carbon atoms and no double or triple bonds; and $CH_3(CH_2)_nCH(OH)-$ or $CH_3(CH_2)_nCH(OH)CH_2-$, wherein n denotes an integer. In another embodiment, R is an alkadienyl having 11-13 carbon atoms. In yet another embodiment, $R_1$ is H and $R_2$ is OH.

In all embodiments, it is preferred that the spicamycin derivative in the composition is 6-[4-deoxy-4-[(2E,4E)-tetradecadienoylglycyl]amino-L-glycero-β-L-manno heptopyranosyl]amino-9H-purine (KRN5500) and has the structure of Formula III.

III

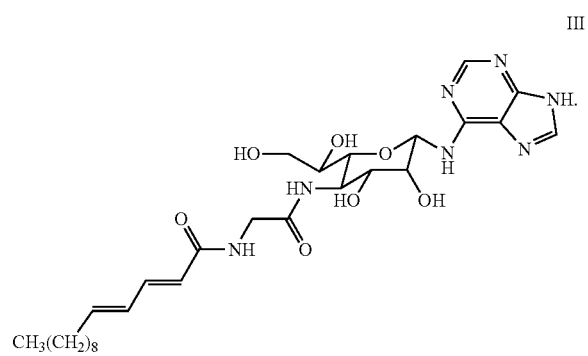

Numerous additional spicamycin derivatives are known in the art (see, e.g., U.S. Pat. Nos. 5,461,036, 5,631,238, 5,905,069, 7,196,071, and 7,375,094, and U.S. patent application Ser. No. 13/122,771, each incorporated herein by reference in its entirety). Exemplary compounds include the following compounds as well as pharmaceutically acceptable salts, prodrugs, and optical isomers thereof:

6-[4'-N—(N'-tridecanoylglycyl)spicaminyl-amino]purine (SPM 9),
6-[4'-N—(N'-tetradecanoylglycyl)spicaminyl-amino]purine (SPM 10),
6-[4'-N—(N'-10-methylundecanoylglycyl)spicaminyl-amino]purine (SPK 9),
6-[4'-N—(N'-11-methyldodecanoylglycyl)spicaminyl-amino]purine (SPK 251),
6-[4'-N—(N'-12-methyltridecanoylglycyl)spicaminyl-amino]purine (SPK 136),
6-[4'-N—(N'-11-dodecenoylglycyl)spicaminyl-amino]purine (SPK 44),
6-[4'-N—(N'-12-tridecenoylglycyl)spicaminyl-amino]purine (SPK 142),
6-[4'-N—(N'-cis-9-tetradecenoylglycyl)spicaminyl-amino]purine (SPK 231),
6-[4'-N—(N'-cis-9-hexadecenoylglycyl)spicaminyl-amino]purine (SPK 148),
6-[4'-N—(N'-trans-2-dodecenoylglycyl)spicaminyl-amino]purine (SPK 86),
6-[4'-N—(N'-trans-2-tetradecenoylglycyl)spicaminyl-amino]purine (SPK 156),
6-[4'-N—(N'-trans-2-hexadecenoylglycyl)spicaminyl-amino]purine (SPK 188),
6-[4'-N—(N'-trans,trans-2,4-dodecadienoyl-glycyl)spicaminyl-amino]purine (SPK 282),
6-[4'-N—(N'-trans,trans-2,4-tridecadienoyl-glycyl)spicaminyl-amino]purine (SPK 281),
6-[4'-N—(N'-trans,trans-2,4-tetradecadienoyl-glycyl)spicaminyl-amino]purine (SPK 241),
6-[4'-N—(N'-11-bromoundecanoylglycyl)spicaminyl-amino]purine (SPK 64),
6-[4'-N—(N'-12-bromododecanoylglycyl)spicaminyl-amino]purine (SPK 152),
6-[4'-N—(N'-13-bromotridecanoylglycyl)spicaminyl-amino]purine (SPK 276),
6-[4'-N—(N'-14-bromotetradecanoylglycyl)spicaminyl-amino]purine (SPK 273),
6-[4'-N—(N'-12-chlorododecanoylglycyl)spicaminyl-amino]purine (SPK 132),
6-[4'-N—(N'-13-chlorotridecanoylglycyl)spicaminyl-amino]purine (SPK 278),
6-[4'-N—(N'-14-chlorotetradecanoylglycyl)spicaminyl-amino]purine (SPK 280),
6-[4'-N—(N'-14-fluorotetradecanoylglycyl)spicaminyl-amino]purine (SPK 279),
6-[4'-N—(N'-15-fluoropentadecanoylglycyl)spicaminyl-amino]purine (SPK 247),
6-[4'-N—(N'-16-fluorohexadecanoylglycyl)spicaminyl-amino]purine (SPK 157),
6-[4'-N—(N'-11-iodoundecanoylglycyl)spicaminyl-amino]purine (SPK 165),
6-[4'-N—(N'-2-chlorohexadecanoylglycyl)spicaminyl-amino]purine (SPK 135),
6-[4'-N—(N'-2-fluorododecanoylglycyl)spicaminyl-amino]purine (SPK 159),
6-[4'-N—(N'-2-fluorohexadecanoylglycyl)spicaminyl-amino]purine (SPK 233),
6-[4'-N—(N'-2,2-difluorotetradecanoylglycyl)-spicaminyl-amino]purine (SPK 182),
6-[4'-N—(N'-2-hydroxyhexadecanoylglycyl)spicaminyl-amino]purine (SPK 112),
6-[4'-N—(N'—(S)-2-hydroxyhexadecanoylglycyl)-spicaminyl-amino]purine (SPK 271),
6-[4'-N—(N'—(R)-3-hydroxytetradecanoylglycyl)-spicaminyl-amino]purine (SPK 270),
6-[4'-N—(N'—(S)-3-hydroxytetradecanoylglycyl)-spicaminyl-amino]purine (SPK 274), 6-[4'-N—(N'-3-hydroxyhexadecanoylglycyl)-spicaminyl-amino]purine (SPK 115),
6-[4'-N—(N'-16-cyanohexadecanoylglycyl)-spicaminyl-amino]purine (SPK 177),
6-[4'-N—(N'-11-phenoxyundecanoylglycyl)-spicaminyl-amino]purine (SPK 422),
6-[4'-N—(N'-12-phenoxydodecanoylglycyl)-spicaminyl-amino]purine (SPK 249),
6-[4'-N—(N'—(R)-2-acetoxyhexadecanoylglycyl)-spicaminyl-amino]purine (SPK 198),
6-[4'-N—(N'-3-acetoxyhexadecanoylglycyl)-spicaminyl-amino]purine (SPK 189),
6-[4'-N—(N'-12-butanesulfonyloxydodecanoylglycyl)-spicaminyl-amino]purine (SPK 232),
6-{4'-N—[N'-11-(2'-thienyl)-10-undecynoylglycyl]-spicaminyl-amino}purine (SPK 262),
6-{4'-N—[N'-11-(3'-thienyl)-10-undecynoylglycyl]-spicaminyl-amino}purine (SPK 263), and
6-{4'-N—[N'-11-(3'-furyl)-10-undecynoylglycyl]-spicaminyl-amino}purine (SPK 266).

Compounds of Formula II can be synthesized using art-known methods, e.g., as disclosed in U.S. Pat. Nos. 5,631,238, 5,461,036, and 5,905,069.

In certain embodiments, a spicamycin derivative can be present in the composition of the invention in an amount of from about 0.01 mg/mL to about 10 mg/mL, from about 0.1 mg/mL to about 5 mg/mL, or from about 2 mg/mL to about 4 mg/mL. The first biocompatible organic solvent can be present in an amount of from about 1 mg/mL to about 500 mg/mL, from about 100 mg/mL to about 450 mg/mL, or from about 250 mg/mL to about 350 mg/mL. The second biocompatible organic solvent can be present in an amount of from about 1 mg/mL to about 1 g/mL, from about 300 mg/mL to about 900 mg/mL, or from about 600 mg/mL to about 700 mg/mL. The surfactant can be present in the composition of the invention in an amount of from about 0.1 mg/mL to about 250 mg/mL, from about 10 mg/mL to about 150 mg/mL, or from about 20 mg/mL to about 100 mg/mL.

In a specific embodiment, the composition of the invention comprises a spicamycin derivative in an amount of from about 2 mg/mL to about 4 mg/mL, the first biocompatible organic solvent in an amount of from about 250 mg/mL to about 350 mg/mL, the second biocompatible organic solvent in an amount of from about 600 mg/mL to about 700 mg/mL, and surfactant in an amount of from about 20 mg/mL to about 100 mg/mL.

In a preferred embodiment, the composition of the invention comprises KRN5500 in an amount of from about 0.01 mg/mL to about 10 mg/mL, ethanol in an amount of from about 1 mg/mL to about 500 mg/mL, propylene glycol in an amount of from about 1 mg/mL to about 1 g/mL, and polysorbate 80 in an amount of from about 0.1 mg/mL to about 250 mg/mL.

In another preferred embodiment, the composition of the invention comprises KRN5500 in an amount of from about 0.01 mg/mL to about 10 mg/mL, ethanol in an amount of from about 1 mg/mL to about 500 mg/mL, propylene glycol in an amount of from about 1 mg/mL to about 1 g/mL, and Lutrol F68 in an amount of from about 0.1 mg/mL to about 250 mg/mL.

In another preferred embodiment, the composition of the invention comprises KRN5500 in an amount of from about 0.1 mg/mL to about 5 mg/mL, ethanol in an amount of from about 100 mg/mL to about 450 mg/mL, propylene glycol in an amount of from about 300 mg/mL to about 900 mg/mL, and polysorbate 80 in an amount of from about 10 mg/mL to about 150 mg/mL.

In another preferred embodiment, the composition of the invention comprises KRN5500 in an amount of from about 0.1 mg/mL to about 5 mg/mL, ethanol in an amount of from about 100 mg/mL to about 450 mg/mL, propylene glycol in an amount of from about 300 mg/mL to about 900 mg/mL, and Lutrol F68 in an amount of from about 10 mg/mL to about 150 mg/mL.

In another preferred embodiment, the composition of the invention comprises KRN5500 in an amount of from about 2 mg/mL to about 4 mg/mL, ethanol in an amount of from about 250 mg/mL to about 350 mg/mL, propylene glycol in an amount of from about 600 mg/mL to about 700 mg/mL, and polysorbate 80 in an amount of from about 20 mg/mL to about 100 mg/mL.

In another preferred embodiment, the composition of the invention comprises KRN5500 in an amount of from about 2 mg/mL to about 4 mg/mL, ethanol in an amount of from about 250 mg/mL to about 350 mg/mL, propylene glycol in an amount of from about 600 mg/mL to about 700 mg/mL, and Lutrol F68 in an amount of from about 10 mg/mL to about 100 mg/mL.

In a most preferred embodiment, the composition of the invention comprises KRN5500 in an amount of about 2 mg/mL, ethanol in an amount of about 293 mg/mL, propylene glycol in an amount of about 640 mg/mL, and polysorbate 80 in an amount of about 20 mg/mL.

In another most preferred embodiment, the composition of the invention comprises KRN5500 in an amount of about 4 mg/mL, ethanol in an amount of about 293 mg/mL, propylene glycol in an amount of about 618 mg/mL, and polysorbate 80 in an amount of about 40 mg/mL.

In another most preferred embodiment, the composition of the invention comprises KRN5500 in an amount of about 5 mg/mL, ethanol in an amount of about 293 mg/mL, propylene glycol in an amount of about 618 mg/mL, and polysorbate 80 in an amount of about 40 mg/mL.

In another most preferred embodiment, the composition of the invention comprises KRN5500 in an amount of about 6 mg/mL, ethanol in an amount of about 293 mg/mL, propylene glycol in an amount of about 618 mg/mL, and polysorbate 80 in an amount of about 40 mg/mL.

In another most preferred embodiment, the composition of the invention comprises KRN5500 in an amount of about 8 mg/mL, ethanol in an amount of about 293 mg/mL, propylene glycol in an amount of about 618 mg/mL, and polysorbate 80 in an amount of about 40 mg/mL.

In another most preferred embodiment, the composition of the invention comprises KRN5500 in an amount of about 2 mg/mL, ethanol in an amount of about 293 mg/mL, propylene glycol in an amount of about 650 mg/mL, and Lutrol F68 in an amount of about 10 mg/mL.

Some of the most preferred embodiments of the composition of the invention are set forth below in Table 1.

TABLE 1

| Formulation Composition | Batch and Formulation Number | | |
|---|---|---|---|
| | 01 | 02 | 03 |
| KRN5500 (mg/mL) | 2 | 2 | 4 |
| Lutrol F68 (mg/mL) | 10 | — | — |

TABLE 1-continued

|  |  | Batch and Formulation Number | | |
|---|---|---|---|---|
|  |  | 01 | 02 | 03 |
| Polysorbate 80 (mg/mL) | | — | 20 | 40 |
| Propylene Glycol (mg/mL) | | 650 | 640 | 618 |
| Ethanol (mg/mL) | | 293 | 293 | 293 |
| Batch Volume (mL) | | 300 | 300 | 200 |
| Fill | (mL/vial) | 5 | 5 | 2.5 |
| | (mg/vial) | 10 | 10 | 10 |
| In-Process Results | | | | |
| Total Compounding Mixing Time (min) | | 69 | 74 | 73 |
| Before Filtration | Assay (mg/mL) | 1.996 | 1.967 | 3.907 |
| | Total Related Substances (%) | 0.59 | 0.44 | 0.49 |
| | Appearance | clear colorless solution | clear colorless solution | clear colorless solution |
| Filtration time (min) | | 5 | 8 | 6 |
| After Filtration | Assay (mg/mL) | 1.986 | 2.007 | 3.919 |
| | Total Related Substances (%) | 0.53 | 0.50 | 0.54 |
| | Appearance | clear colorless solution | clear colorless solution | clear colorless solution |
| | Density (g/mL) | 0.954 | 0.955 | 0.955 |
| Target Filling weight (g) | | 4.770 | 4.775 | 2.388 |
| Filling Time (min) | | 50 | 38 | 25 |
| Crimping Time (min) | | 20 | 33 | 25 |
| Total vials crimped | | 53 | 54 | 66 |
| Appearance | After 5 min sonication | Clear solution | Clear solution | Clear solution |
| | After single −20 freeze/thaw cycle | Clear solution | Clear solution | Clear solution |
| Stability study 1 vial of finished product at 60° C. for 2 weeks | Appearance | clear colorless solution | clear colorless solution | clear colorless solution |
| | Assay (mg/mL) | 1.697 | 0.320 | 1.293 |
| | Total Related Substances (%) | 17.21 | 62.79 | 42.06 |

In another specific embodiment, the composition of the invention comprises a spicamycin derivative in an amount of from about 0.01 mg/mL to about 0.03 mg/mL, the first biocompatible organic solvent in an amount of from about 2 mg/mL to about 3 mg/mL, the second biocompatible organic solvent in an amount of from about 4 mg/mL to about 7 mg/mL, and surfactant in an amount of from about 0.2 mg/mL to about 0.5 mg/mL.

In a preferred embodiment, where a concentrated solution of the invention is diluted into an intravenous infusion liquid or diluent at a ratio of 1:100 to prepare an intravenous solution, the intravenous solution comprises KRN5500 in an amount of about 0.04 mg/mL, ethanol in an amount of about 2.93 mg/mL, propylene glycol in an amount of about 6.18 mg/mL, and polysorbate 80 in an amount of about 0.40 mg/mL.

In another preferred embodiment, where a concentrated solution of the invention is diluted into an intravenous infusion liquid or diluent at a ratio of 1:10 to prepare an intravenous solution, the intravenous solution comprises KRN5500 in an amount of about 0.4 mg/mL, ethanol in an amount of about 29.3 mg/mL, propylene glycol in an amount of about 61.8 mg/mL, and polysorbate 80 in an amount of about 4.0 mg/mL.

In another preferred embodiment, where a concentrated solution of the invention is diluted into an intravenous infusion liquid or diluent at a ratio of 1:30 to prepare an intravenous solution, the intravenous solution comprises KRN5500 in an amount of about 1.2 mg/mL, ethanol in an amount of about 87.9 mg/mL, propylene glycol in an amount of about 185.4 mg/mL, and polysorbate 80 in an amount of about 12.0 mg/mL.

In further embodiments of the composition, the total excipient exposure of the first biocompatible organic solvent is in an amount of from about 10 mg/kg to about 20 mg/kg, the total excipient exposure of the second biocompatible organic solvent is in an amount of from about 25 mg/kg to about 50 mg/kg, and the total excipient exposure of the surfactant is in an amount of from about 1 mg/kg to about 4 mg/kg. In such embodiments, total excipient exposure assumes a dose of the spicamycin derivative as 6.4 mg/m$^2$, a body surface area of 1.7 m$^2$, a body mass of 70 kg, and an infusion volume of 500 mL.

The composition of the invention is preferably a spicamycin derivative dissolved in organic solvent to form a liquid that is substantially free of particulates and essentially free of mono-ethanolamine. Preferably, there are substantially no particulates present after about two weeks, about 6 months, about 1 year, about 5 years, about 10 years, or longer, after the composition is formulated. As used herein, "substantially free of particulates" is considered to mean the number and size of particulates known by those of ordinary skill in the art to be in accordance with the regulations established by the U.S. Pharmaceutical Convention in General Chapter <788> Particulate Matter in Injections and the USP Particle Count Reference Standard.

In the most preferred embodiments of the invention, wherein the volume of the composition is 100 mL or less, the composition comprises particulates in an amount of from about 0-6000 particles, or from about 0-1000 particles, or from about 0-500 particles, or from about 0-100 particles, or from about 0-50 particles, or from about 0-10 particles, or 0 particles, wherein the particle size is at least 10 µm. In another most preferred embodiment of the invention, wherein the volume of the composition is 100 mL or less, the composition comprises particulates in an amount of from about 0-600 particles, or from about 0-300 particles, or from about 0-100 particles, or from about 0-50 particles, or from about 0-10 particles, or 0 particles, wherein the particle size is at least 25 µm.

In another most preferred embodiment of the invention, wherein the volume of the composition is more than 100 mL, the composition comprises particulates in an amount of from about 0-25 particles/mL, or from about 0-10 particles/mL, or from about 0-5 particles/mL, or from about 0-2 particles/mL, or 0 particles/mL, wherein the particle size is at least 10 µm. In another most preferred embodiment of the invention, wherein the volume of the composition is more than 100 mL, the composition comprises particulates in an amount of from about 0-3 particles/mL, or from about 0-2 particles/mL, or from about 0-1 particles/mL, or 0 particles/mL, wherein the particle size is at least 25 µm.

In certain embodiments of the invention, where the volume of the composition is 100 mL or less, the composition can comprise particulates in an amount of from about 6000 particles to about 12,000 particles, wherein the particles are at least 10 µm in size. In another such embodiment, the composition can comprise particulates in an amount of from about 600 particles to about 1200 particles, wherein the particles are at least 25 µm in size.

In other embodiments of the invention, where the volume of the composition is greater than 100 mL, the composition can comprise particulates in an amount of from about 25 particles/mL to about 50 particles/mL, wherein the particles are at least 10 µm in size. In another such embodiment, the composition can comprise about 3 particles/mL to about 6 particles/mL, wherein the particles are at least 25 µm in size.

Additionally, the composition of the invention can be "substantially free" of mono-ethanolamine or DMAC, wherein "substantially free" is defined as having no more than a trace amount of mono-ethanolamine or DMAC in the composition. In the most preferred embodiments of the invention, the composition is "essentially free" of mono-ethanolamine or DMAC, wherein "essentially free" specifically means that the composition does not comprise any mono-ethanolamine or any DMAC.

In one embodiment, the composition of the invention comprises a spicamycin derivative described herein and further comprises a second analgesic or drug. In particular embodiments, the second analgesic or drug is an anti-inflammatory drug.

The invention also provides a method for preparing the concentrated solutions described herein comprising a spicamycin derivative. The method comprises the steps of contacting a spicamycin derivative of the invention with a first biocompatible organic solvent, as described herein, and a surfactant to form a first composition. The first composition is then contacted with a second biocompatible organic solvent, as described herein, to form a concentrated solution that is substantially free of particulates and is essentially free of mono-ethanolamine and/or DMAC. The method can further comprise the step of filtering the concentrated solution. In additional embodiments, the spicamycin derivative, the first biocompatible organic solvent, the second biocompatible organic solvent, and the surfactant can be contacted together in any order to achieve the concentrated solution of the method. In one particular embodiment, the spicamycin derivative is first contacted with the second biocompatible organic solvent, then contacted with the first biocompatible organic solvent, and finally contacted with the surfactant.

In certain embodiments of the invention, the concentrated solution is substantially free of particulates and essentially free of mono-ethanolamine. Preferably, there are substantially no particulates present in the concentrated solution after about two weeks, after about 1 year, after about 10 years or longer, after the concentrated solution is formulated.

In the most preferred embodiments of the invention, wherein the volume of the concentrated solution is 100 mL or less, the concentrated solution comprises particulates in an amount of from about 0-6000 particles, or from about 0-1000 particles, or from about 0-500 particles, or from about 0-100 particles, or from about 0-50 particles, or from about 0-10 particles, or 0 particles, wherein the particle size is at least 10 µm. In another most preferred embodiment of the invention, wherein the volume of the concentrated solution is 100 mL or less, the concentrated solution comprises particulates in an amount of from about 0-600 particles, or from about 0-300 particles, or from about 0-100 particles, or from about 0-50 particles, or from about 0-10 particles, or 0 particles, wherein the particle size is at least 25 µm.

In other embodiments of the invention, where the volume of the concentrated solution is less than 100 mL, the concentrated solution can comprise particulates in an amount of from about 6000 particles to about 12,000 particles, wherein the particles are at least 10 µm in size. In another such embodiment, the composition can comprise particulates in an amount of from about 600 particles to about 1200 particles, wherein the particles are at least 25 µm in size.

Additionally, the concentrated solution of the invention is substantially free of mono-ethanolamine or DMAC. In the most preferred embodiments of the invention, the concentrated solution is essentially free of mono-ethanolamine or DMAC.

The invention also provides methods for preparing the intravenous solutions described herein comprising a spicamycin derivative. The method comprises the step of contacting the concentrated solution produced by the method above with an intravenous infusion liquid or diluent, wherein the resulting intravenous solution is substantially free of particulates.

In particular embodiments of the method, the aqueous intravenous liquid or diluent is selected from the group consisting of 0.9% sodium chloride, 5% dextrose, and Lactated Ringers solution. The compositions of these aqueous intravenous liquids or diluents are well-known in the art. In further embodiments, the concentrated solution can be diluted into the aqueous intravenous infusion liquid or diluent at a ratio selected from the group consisting of 1:10 (v/v), 1:30 (v/v), and 1:100 (v/v).

In the most preferred embodiment of the invention, wherein the volume of the intravenous solution is more than 100 mL, the intravenous solution comprises particulates in an amount of from about 0-25 particles/mL, or from about 0-10 particles/mL, or from about 0-5 particles/mL, or from about 0-2 particles/mL, or 0 particles/mL, wherein the particle size is at least 10 µm. In another most preferred embodiment of the invention, wherein the volume of the intravenous solution is more than 100 mL, the intravenous solution comprises particulates in an amount of from about 0-3 particles/mL, or from about 0-2 particles/mL, or from about 0-1 particles/mL, or 0 particles/mL, wherein the particle size is at least 25 µm.

In certain embodiments of the invention, the intravenous solution can comprise particulates in an amount of from about 25 particles/mL to about 50 particles/mL, wherein the particles are at least 10 µm in size. In other embodiments, the intravenous solution can comprise particulates in an amount of from about 3 particles/mL to about 6 particles/mL, wherein the particles are at least 25 µm in size.

In a further embodiment, the intravenous solution produced by the method comprises a spicamycin derivative described herein and further comprises a second analgesic or drug. In particular embodiments, the second analgesic or drug is an anti-inflammatory drug.

The invention also provides methods for treating or preventing pain or neurotoxicity in a subject, comprising administering to a subject in need thereof a preventative or treatment effect amount of the compositions of the invention that comprise a spicamycin derivative described herein. In one embodiment, the compositions of the invention are administered in a combination formulation further comprising a second analgesic or drug. In particular embodiments, the second analgesic or drug is an anti-inflammatory drug.

The spicamycin derivatives of the invention include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

The spicamycin derivatives of the invention also include those having quaternization of any basic nitrogen-containing group therein.

The discussion herein is, for simplicity, provided without reference to stereoisomerism. Those skilled in the art will appreciate that the spicamycin derivatives of the invention (e.g., those of Formula II) can contain one or more asymmetric centers and thus occur as racemates and racemic mixtures, single optical isomers, individual diastereomers, and diastereomeric mixtures. All such isomeric forms of these compounds are expressly included in the present invention.

Similarly, the spicamycin derivatives of the invention containing a double bond can exist in the form of geometric isomers, which can be readily separated and recovered by conventional procedures. Such isomeric forms are included in the scope of this invention.

Further, the invention includes prodrugs of the spicamycin derivatives of the invention (e.g., those of Formula II) that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

In one embodiment of the invention, a spicamycin derivative described herein is used to treat or prevent pain in a subject. Pain can be defined as any type of nociceptive pain, somatic pain, visceral pain, or neuropathic pain. In one embodiment, the pain can be due to a neuropathy, e.g., neuropathic pain. The neuropathy can be any form of neuropathy. In some embodiments, the neuropathy is selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post-surgical pain syndrome, post mastectomy syndrome, post thoracotomy syndrome, phantom pain, nerve root avulsion, post radiation neuropathy, repetitive movement nerve injury, repetitive stress injury, and post injury neuropathy. In one embodiment, the pain that is treated or prevented includes nociceptive pain. In another embodiment, the pain that is treated or prevented excludes nociceptive pain.

In an additional embodiment, where the spicamycin derivative of the invention is used to treat or prevent a chemotherapy-induced neuropathy (CIN) in a subject, the CIN may be a chemotherapy-induced peripheral neuropathy (CIPN). CIPN is attributable to a broad variety of antineoplastic agents. CIPN-inducing agents generally come from six principal drug classes including platinum agents, taxanes, vinca alkaloids, boronic acid derivatives, phthaloyl derivatives and epothilones. Cisplatin, paclitaxel, docetaxel, and vincristine are particular offenders.

CIPN can manifest as any one of at least twenty distinct symptoms affecting sensory, motor, and autonomic systems. Sensory symptoms include pain, tingling, numbness, instability when standing or walking, problems distinguishing temperature, and hearing problems. Motor symptoms include cramps, difficulty writing, difficulty manipulating small objects, and weakness. Autonomic symptoms include vision changes, dizziness after changing position, and erection disorders. Commonly used indices for the measurement of CIPN include the National Cancer Institute-Common Toxicity Criteria (NCI-CTC) score (see, Argyriou et al., *Crit. Rev Oncol/Hematol* 2012; 85:51-77) and the Numeric Rating Scale (NRS), a method for assessing pain that is well-known to those of ordinary skill in the art.

In a particular embodiment, the CIPN treated by the spicamycin derivative of the invention is painful chemotherapy-induced peripheral neuropathy (painful CIPN). Painful CIPN can be a debilitating condition that currently has no validated preventative or treatment (see, Wolf et al., *Eur J Cancer* 2008; 44:1507-1515; Kaley and DeAngelis, *Brit J Haematol* 2009; 145:3-14). In further embodiments, the painful CIPN treated by the spicamycin derivative of the invention can be either painful acute chemotherapy-induced peripheral neuropathy (painful ACIPN) or painful chronic chemotherapy-induced peripheral neuropathy (painful CCIPN).

Painful ACIPN commonly occurs during administration of a variety of chemotherapeutic agents and resolves spontaneously within days or up to about 12 weeks after cessation of chemotherapy. Painful ACIPN can be caused by commonly used chemotherapeutic agents including carboplatin, vincristine, vinblastine, and ixabepalone. Painful ACIPN induced by these agents has been demonstrated to be reversible when drug administration ends (see, Alberts et al., *J Clin Oncol* 1992; 10:706-717; Postma et al., *J Neuro-Oncol.* 1993; 15:23-27; Argyriou et al., *Crit. Rev Oncol/Hematol* 2012; 85:51-77; Kannarkat et al., *Curr Opin Neurol.* 2007; 20:719-725).

By contrast, painful CCIPN is defined as neuropathic pain associated with the administration of chemotherapeutic agents which fails to resolve by about twelve weeks after cessation of the last cycle of chemotherapy. Painful CCIPN commonly results from the administration of any one of six important chemotherapeutic agents that are widely used in the treatment of a variety of cancers. These chemotherapeutic agents include cisplatin, oxaliplatin, paclitaxel, docetaxel, bortezomib, and thalidomide. Painful CCIPN can be caused by these chemotherapeutic agents alone or a combination of agents.

In another embodiment of the invention, a spicamycin derivative described herein is used to treat or prevent neurotoxicity in a subject. The neurotoxicity can be any type of neurotoxicity including, but not limited to, hearing loss, allodynia, pain, numbness, tingling, burning, muscle weakness, and dizziness.

In another embodiment of the invention, a spicamycin derivative described herein is administered to the subject as needed to treat or prevent pain or neurotoxicity. The spicamycin derivative can be administered continuously or intermittently. In one embodiment, the spicamycin derivative is administered to the subject more than once a day or once every 1, 2, 3, 4, 5, 6, or 7 days. In another embodiment, the spicamycin derivative is administered to the subject no more than once a week, e.g., no more than once every two weeks, once a month, once every two months, once every three months, once every four months, once every five months, once every six months, or longer. In a further embodiment, the spicamycin derivative is administered using two or more different schedules, e.g., more frequently initially (for example to build up to a certain level, e.g., once a day or more) and then less frequently (e.g., once a week or less). The spicamycin derivative can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more prior to the onset of pain (e.g., prior to an event that is likely to induce pain). The compound can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more after the onset of pain or an event likely to induce pain. In other embodiments, the spicamycin derivative can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

The spicamycin derivative described herein can be administered to a subject for various durations of time including about 5 minutes, 10 minutes, 30 minutes, 45 minutes, 1 hour, 2 hours, 4 hours, 6 hours, 8 hours, 12 hours, 18 hours, 24 hours or longer.

In one embodiment, the composition of the invention can be delivered to the subject by parenteral administration. In such an embodiment, the route can be intravenous, intramuscular, sub-cutaneous, intrathecal or intraarterial administration. The composition of the invention can be delivered to the subject at a dose that is effective to treat and/or prevent pain or neurotoxicity. The effective dosage will depend on many factors including the gender, age, weight, and general physical condition of the subject, the severity of the pain, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, *The Science and Practice of Pharmacy* (21$^{st}$ ed. 2005)). In one embodiment, the composition of the invention is administered at a dose of about 0.2 to about 10.0 mg/m$^2$, e.g., about 0.6 to about 4.0 mg/m$^2$, about 1.0 to about 3.0 mg/m$^2$, or about 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 mg/m$^2$. In some instances, the dose can be even lower, e.g., as low as 0.1, 0.05, 0.01, 0.005, or 0.001 mg/m$^2$ or lower. In some instances, the dose can be even higher, e.g., as high as 20, 50, 100, 500, or 1000 mg/m$^2$ or higher. The present invention encompasses every sub-range within the cited ranges and amounts.

In one embodiment of the invention, the subject is one that has developed a neuropathy and the composition of the invention is administered to the subject after the development of neuropathy in order to treat the pain. In another embodiment, the subject is one that has not developed a neuropathy and the composition of the invention is administered to the subject to prevent the occurrence of pain. In one embodiment, the subject is one that is undergoing an event that is likely to result in the development of neuropathy. The composition of the invention can be delivered to the subject prior to the event occurring, concurrently with the event, and/or after the event occurs but before the development of pain. Events that are likely to result in the development of neuropathy are well known and include, without limitation, surgery (e.g., amputation, mastectomy, thoracotomy), traumatic nerve damage, radiation treatment, and chemotherapy.

In another embodiment of the invention, the subject is currently undergoing, will be undergoing, and/or has undergone chemotherapy treatment with one or more chemotherapeutic agents that are known or suspected to induce neuropathy and the spicamycin derivative is administered to prevent and/or treat pain. Chemotherapeutic agents known to induce neuropathy include, without limitation, vinca alkaloids (e.g., vinblastine, vincristine, vindesine, vinflunine, or vinorelbine), taxanes (e.g., paclitaxel or docetaxel), platinum-based compounds (e.g., cisplatin, carboplatin, nedaplatin, triplatin tetranitrate, satraplatin, or oxaliplaten), boronic acid (bortezomib), pthaloyl derivatives (thalidomide, or lenolidamide), and epotilones (ixabepalone).

In one embodiment of the invention, the composition of the invention is delivered to a subject concurrently with a second analgesic or drug. The second analgesic or drug can be delivered in the same composition as the spicamycin derivative or in a separate composition. The second analgesic or drug can be delivered to the subject on a different schedule or by a different route as compared to the spicamycin derivative. The second analgesic or drug can be any agent that provides a benefit to the subject. Further agents include, without limitation, chemotherapeutic agents, antiemetic agents, analgesic agents (e.g., opioids and/or systemic local anesthetics), anti-inflammatory agents, and peroxisome proliferator-activated receptor (PPAR) agonists, e.g., PPAR δ agonists.

Examples of chemotherapeutic agents include, without limitation, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfarnide, ilmofosine, interleukin II (including recombinant interleukin II or rIL2), interferon alfa-2a, interferon alfa-2b, interferon alfa-n1, interferon alfa-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other chemotherapeutic agents include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; prostatic carcinoma antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of antiemetic agents include, without limitation, metoclopromide, domperidone, prochlorperazine, promethazine, chlorpromazine, trimethobenzamide, odansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

Examples of analgesic agents include, without limitation, the opioids allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, and tramadol.

Examples of anti-inflammatory agents include, without limitation, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, celecoxib, rofecoxib, and corticosteroids (e.g., prednisone, methylprednisolone, dexamethasone).

Examples of PPAR δ agonists include, without limitation, those disclosed in U.S. Pat. Nos. 6,713,514, 6,677,298, 6,462,046, 5,925,657, 5,326,770 EP 1586573, U.S. 20050245589, and WO 2005049572 and in Combs et al., *J. Neurosci.* 20:558 (2000), including without limitation GW 501516, GW 610742, L-165041, DB959, GFT-505, MTX-8025, HPP-593, KD-3010, and carbaprostacyclin.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has pain (e.g., neuropathic pain and/or nociceptive pain and/or non-neuropathic inflammatory pain) and/or is anticipated to experience pain. In other embodiments, the subject used in the methods of the invention is an animal model of pain.

The subject can be a subject "in need of" the methods of the present invention, e.g., in need of the therapeutic and/or prophylactic effects of the inventive methods. For example, the subject can be a subject that is experiencing pain (e.g., neuropathic pain and/or nociceptive pain and/or non-neuropathic inflammatory pain) and/or is anticipated to experience pain, and the methods and compositions of the invention are used for therapeutic and/or prophylactic treatment.

The subject can further be a laboratory animal, e.g., an animal model of pain (see, e.g., Kim et al., *Pain* 50:355 (1992); Bennett et al., *Pain* 33:87 (1988); U.S. Patent Publication 2004/0038927).

The composition of the invention and the spicamycin derivatives described herein can be formulated for administration in a pharmaceutical vehicle, biocompatible formulation, or biocompatible solvent, in accordance with known techniques. See, e.g., Remington, *The Science And Practice of Pharmacy* (21$^{st}$ ed. 2005). The vehicle, formulation, or solvent must be acceptable in the sense of being compatible with any other ingredients in the formulation and must not be deleterious to the patient. The formulations of the invention include parenteral routes of administration, including intravenous, intramuscular, sub-cutaneous, intrathecal or intraarterial administration, although the most suitable route in any given case will depend on the nature and severity of the condition being treated and on the nature of the particular active compound which is being used.

The compositions of the invention which are suitable for parenteral administration include, but are not limited to, sterile aqueous and non-aqueous injection solutions that are preferably isotonic or hypertonic with the blood of the intended recipient. These compositions can contain anti-oxidants, buffers, bacteriostats and solutes which render the formulation isotonic with the blood of the intended recipient. Aqueous sterile suspensions can include suspending agents and thickening agents. The formulations can be presented in unit\dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions can be prepared from sterile powders, granules and tablets of the kind previously described. For example, in one aspect of the present invention, there is provided an injectable, stable, sterile composition comprising the composition of the invention in a unit dosage form in a sealed container. The composition of the invention can also be provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the compound. When the compounds of the invention are substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

In certain embodiments, the compositions of the invention can contain further additives including, but not limited to, pH-adjusting additives, osmolarity adjusters, tonicity adjusters, anti-oxidants, reducing agents, and preservatives. Useful pH-adjusting agents include acids, such as hydrochloric acid, bases or buffers, such as sodium lactate, sodium acetate, sodium phosphate, sodium citrate, sodium borate, or sodium gluconate. Further, the compositions of the invention can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The following are specific embodiments of the subject matter described herein:

1. A composition comprising:
   a) a spicamycin derivative of Formula II:

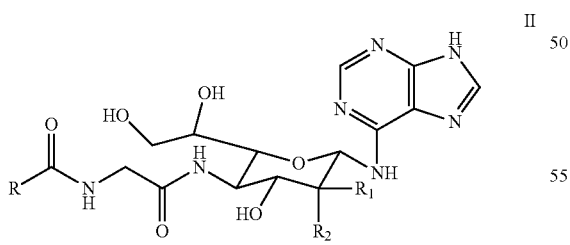

wherein $R_1$ and $R_2$ are different from each other and represent H or OH, and R represents a substituted or unsubstituted alkyl, alkenyl, alkynyl, or cycloalkyl;
   b) a first biocompatible organic solvent that solubilizes said spicamycin derivative;
   c) a second biocompatible organic solvent that is miscible with said first biocompatible organic solvent and solubilizes said spicamycin derivative; and
   d) a surfactant soluble in a mixture of said first biocompatible organic solvent and said second biocompatible organic solvent;
wherein said composition is essentially free of mono-ethanolamine.

2. The composition of embodiment 1, further comprising an aqueous intravenous liquid or diluent.

3. The composition of embodiment 2, wherein said aqueous intravenous liquid or diluent is selected from the group consisting of:
   a) 0.9% sodium chloride;
   b) 5% dextrose; and
   c) Lactated Ringers solution.

4. The composition of embodiment 1 or embodiment 2, wherein said composition is substantially free of particulates.

5. The composition of embodiment 1 or embodiment 2, wherein said composition is substantially free of particulates for about two weeks after said composition is formulated.

6. The composition of embodiment 1 or embodiment 2, wherein said composition is substantially free of particulates for at least 1 year after said composition is formulated.

7. The composition of embodiment 1, wherein said composition is essentially free of N,N-dimethyl acetamide (DMAC).

8. The composition of embodiment 1, wherein said spicamycin derivative is a compound of Formula II and R is selected from the group consisting of:
   a) a linear alkenyl having 11-13 carbon atoms;
   b) a linear, unsubstituted alkyl having 11-13 carbon atoms and no double or triple bonds;
   c) a linear haloalkyl having 10-15 carbon atoms;
   d) $CH_3(CH_2)_nCH(OH)$— or $CH_3(CH_2)_{n-1}CH(OH)CH_2$—, wherein n denotes an integer from 9-13;
   e) an alkyl having 10-15 carbon atoms substituted with an azide group or a cyano group;
   f) a linear alkyl having 10-13 carbon atoms substituted with a phenoxy group or a halogen-substituted phenoxy group;

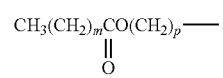

g)

wherein m denotes an integer from 0-2 and p denotes an integer from 9-14;

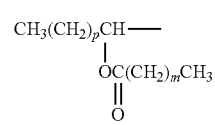

h)

wherein m denotes an integer from 0-2 and p denotes an integer from 8-13;

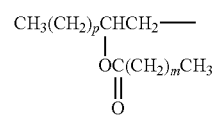

i)

wherein m denotes an integer from 0-2 and p denotes an integer from 10-15;

j) $CH_3(CH_2)_mSO_2O(CH_2)_p-$, wherein m denotes an integer from 0-3 and p denotes an integer from 9-14;

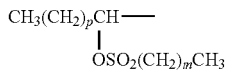  k)

wherein m denotes an integer from 0-3 and p denotes an integer from 10-15;

  l)

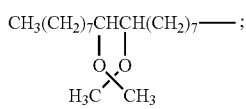  m)

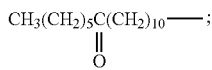  n)

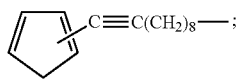  o)

and
p) a linear alkadienyl having 11-13 carbon atoms.

9. The composition of embodiment 8, wherein R is selected from the group consisting of:
   a) a linear alkenyl having 11-13 carbon atoms;
   b) a linear, unsubstituted alkyl having 11-13 carbon atoms and no double or triple bonds; and
   c) $CH_3(CH_2)_nCH(OH)-$ or $CH_3(CH_2)_nCH(OH)CH_2-$, wherein n denotes an integer.

10. The composition of embodiment 8, wherein R is an alkadienyl having 11-13 carbon atoms.

11. The composition of embodiment 8, wherein $R_1$ is H and $R_2$ is OH.

12. The composition of embodiment 8, wherein said spicamycin derivative is 6-[4-deoxy-4-[(2E,4E)-tetradecadienoylglycyl]amino-L-glycero-β-L-manno heptopyranosyl]amino-9H-purine (KRN5500) and has the following structure:

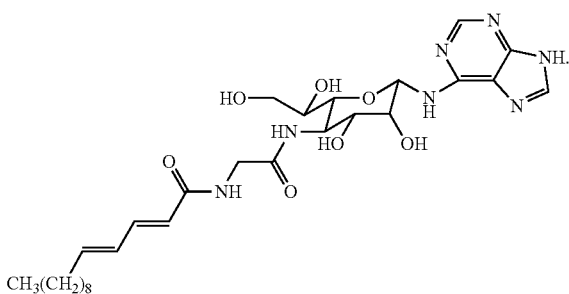

13. The composition of embodiment 1, wherein said spicamycin derivative is present in an amount of from about 0.01 mg/mL to about 10 mg/mL.

14. The composition of embodiment 1, wherein said spicamycin derivative is present in an amount of from about 0.1 mg/mL to about 5 mg/mL.

15. The composition of embodiment 1, wherein said spicamycin derivative is present in an amount of from about 2 mg/mL to about 4 mg/mL.

16. The composition of embodiment 1, wherein said first biocompatible organic solvent is present in an amount of from about 1 mg/mL to about 500 mg/mL.

17. The composition of embodiment 1, wherein said first biocompatible organic solvent is present in an amount of from about 100 mg/mL to about 450 mg/mL.

18. The composition of embodiment 1, wherein said first biocompatible organic solvent is present in an amount of from about 250 mg/mL to about 350 mg/mL.

19. The composition of embodiment 1, wherein said second biocompatible organic solvent is present in an amount of from about 1 mg/mL to about 1 g/mL.

20. The composition of embodiment 1, wherein said second biocompatible organic solvent is present in an amount of from about 300 mg/mL to about 900 mg/mL.

21. The composition of embodiment 1, wherein said second biocompatible organic solvent is present in an amount of from about 600 mg/mL to about 700 mg/mL.

22. The composition of embodiment 1, wherein said surfactant is present in an amount of from about 0.1 mg/mL to about 250 mg/mL.

23. The composition of embodiment 1, wherein said surfactant is present in an amount of from about 10 mg/mL to about 150 mg/mL.

24. The composition of embodiment 1, wherein said surfactant is present in an amount of from about 20 mg/mL to about 100 mg/mL.

25. The composition of embodiment 1, wherein:
   a) said spicamycin derivative is present in an amount of from about 2 mg/mL to about 4 mg/mL;
   b) said first biocompatible organic solvent is present in an amount of from about 250 mg/mL to about 350 mg/mL;
   c) said second biocompatible organic solvent is present in an amount of from about 600 mg/mL to about 700 mg/mL; and
   d) said surfactant is present in an amount of from about 20 mg/mL to about 100 mg/mL.

26. The composition of embodiment 1, wherein:
   a) said spicamycin derivative is present in an amount of from about 0.01 mg/mL to about 0.03 mg/mL;
   b) said first biocompatible organic solvent is present in an amount of from about 2 mg/mL to about 3 mg/mL;
   c) said second biocompatible organic solvent is present in an amount of from about 4 mg/mL to about 7 mg/mL; and
   d) said surfactant is present in an amount of from about 0.2 mg/mL to about 0.5 mg/mL.

27. The composition of embodiment 1, further comprising a second analgesic or drug.

28. The composition of embodiment 27, wherein said second analgesic or drug is an anti-inflammatory drug.

29. The composition of any one of embodiments 1-28, wherein said first biocompatible organic solvent is selected from the group consisting of:
   a) ethanol; and
   b) t-butanol.

30. The composition of embodiment 29, wherein said first biocompatible organic solvent is ethanol.

31. The composition of any one of embodiments 1-30, wherein said second biocompatible organic solvent is selected from the group consisting of:
   a) propylene glycol;
   b) glycerin;
   c) polyethylene glycol; and
   d) polypropylene glycol.

32. The composition of embodiment 31, wherein said second biocompatible organic solvent is propylene glycol.

33. The composition of any one of embodiments 1-32, wherein said surfactant is selected from the group consisting of:
   a) polysorbate;
   b) a poloxamer;
   c) n-dodecyl-b-maltoside;
   d) tocopheryl-polyethylene glycol succinate;
   e) polyethylene glycol;
   f) a polyoxyl;
   g) Solutol;
   h) Pluronics;
   i) sodium dodecyl sulfate;
   j) SPAN; and
   k) octoxynol-9.

34. The composition of embodiment 33, wherein said surfactant is polysorbate.

35. The composition of any one of embodiments 1-34, wherein said composition comprises:
   a) KRN5500 in an amount of about 4 mg/mL;
   b) ethanol in an amount of about 293 mg/mL;
   c) propylene glycol in an amount of about 618 mg/mL; and
   d) polysorbate 80 in an amount of about 40 mg/mL.

36. A method for preparing a concentrated solution, said method comprising:
   a) contacting a spicamycin derivative of Formula II:

[Formula II structure]

with a first biocompatible organic solvent that solubilizes said spicamycin derivative, and a surfactant soluble in said first biocompatible organic solvent, to form a first composition, wherein $R_1$ and $R_2$ are different from each other and represent H or OH, and R represents a substituted or unsubstituted alkyl, alkenyl, alkynyl, or cycloalkyl; and
      b) contacting said first composition with a second biocompatible organic solvent that is miscible with said first biocompatible organic solvent to form said concentrated solution;
   wherein said concentrated solution is substantially free of particulates, and wherein said concentrated solution is essentially free of mono-ethanolamine.

37. The method of embodiment 36, further comprising the step of filtering said concentrated solution of b).

38. The method of embodiment 36, wherein said concentrated solution forms substantially no particulates when diluted into an aqueous intravenous liquid or diluent.

39. The method of embodiment 36, wherein said concentrated solution is substantially free of particulates for about two weeks after said concentrated solution is formulated.

40. The method of embodiment 36, wherein said concentrated solution is substantially free of particulates for at least 1 year after said concentrated solution is formulated.

41. The method of embodiment 36, wherein said concentrated solution is essentially free of N,N-dimethyl acetamide (DMAC).

42. The method of embodiment 36, wherein said spicamycin derivative is a compound of Formula II and R is selected from the group consisting of:

a) a linear alkenyl having 11-13 carbon atoms;
b) a linear, unsubstituted alkyl having 11-13 carbon atoms and no double or triple bonds;
c) a linear haloalkyl having 10-15 carbon atoms;
d) $CH_3(CH_2)_nCH(OH)-$ or $CH_3(CH_2)_{n-1}CH(OH)CH_2-$, wherein n denotes an integer from 9-13;
e) an alkyl having 10-15 carbon atoms substituted with an azide group or a cyano group;
f) a linear alkyl having 10-13 carbon atoms substituted with a phenoxy group or a halogen-substituted phenoxy group;

g) $CH_3(CH_2)_mCO(CH_2)_p-$
         $\parallel$
         $O$ wherein m denotes an integer from 0-2 and p denotes an integer from 9-14;

h) $CH_3(CH_2)_pCH-$
    $\phantom{CH_3(CH_2)_p}|$
    $\phantom{CH_3(CH_2)_p}OC(CH_2)_mCH_3$
    $\phantom{CH_3(CH_2)_pO}\parallel$
    $\phantom{CH_3(CH_2)_pO}O$ wherein m denotes an integer from 0-2 and p denotes an integer from 8-13;

i) $CH_3(CH_2)_pCHCH_2-$
    $\phantom{CH_3(CH_2)_p}|$
    $\phantom{CH_3(CH_2)_p}OC(CH_2)_mCH_3$
    $\phantom{CH_3(CH_2)_pO}\parallel$
    $\phantom{CH_3(CH_2)_pO}O$ wherein m denotes an integer from 0-2 and p denotes an integer from 10-15;

j) $CH_3(CH_2)_mSO_2O(CH_2)_p-$, wherein m denotes an integer from 0-3 and p denotes an integer from 9-14;

k) $CH_3(CH_2)_pCH-$
    $\phantom{CH_3(CH_2)_p}|$
    $\phantom{CH_3(CH_2)_p}OSO_2(CH_2)_mCH_3$ wherein m denotes an integer from 0-3 and p denotes an integer from 10-15;

l) $CH_3Si(CH_2)_{10}-$ or $CH_3Si-C\equiv C-(CH_2)_8-$;

m) $CH_3(CH_2)_7CHCH(CH_2)_7-$;
    with dioxolane bearing two $CH_3$ groups n) $CH_3(CH_2)_5C(CH_2)_{10}-$;
         $\parallel$
         $O$ o) cyclopentadienyl$-C\equiv C(CH_2)_8-$;

and
p) a linear alkadienyl having 11-13 carbon atoms.

43. The method of embodiment 36, wherein R is selected from the group consisting of:
   a) a linear alkenyl having 11-13 carbon atoms;
   b) a linear, unsubstituted alkyl having 11-13 carbon atoms and no double or triple bonds; and
   c) $CH_3(CH_2)_nCH(OH)-$ or $CH_3(CH_2)_nCH(OH)CH_2-$, wherein n denotes an integer.

44. The method of embodiment 36, wherein R is an alkadienyl having 11-13 carbon atoms.

45. The method of embodiment 36, wherein $R_1$ is H and $R_2$ is OH.

46. The method of embodiment 36, wherein said spicamycin derivative is 6-[4-deoxy-4-[(2E,4E)-tetradecadienoylglycyl]amino-L-glycero-β-L-manno heptopyranosyl]amino-9H-purine (KRN5500) and has the following structure:

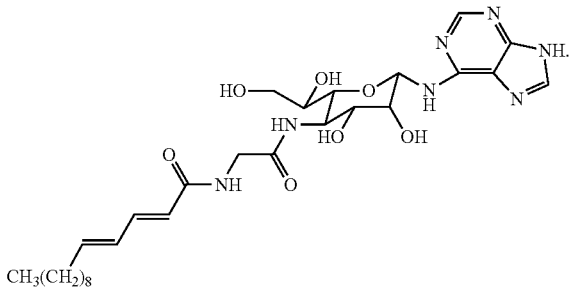

47. The method of embodiment 36, wherein said spicamycin derivative is present in said concentrated solution in an amount of from about 1 mg/mL to about 5 mg/mL.

48. The method of embodiment 36, wherein said spicamycin derivative is present in said concentrated solution in an amount of from about 2 mg/mL to about 4 mg/mL.

49. The method of embodiment 36, wherein said first biocompatible organic solvent is present in said concentrated solution in an amount of from about 100 mg/mL to about 500 mg/mL.

50. The method of embodiment 36, wherein said first biocompatible organic solvent is present in said concentrated solution in an amount of from about 150 mg/mL to about 450 mg/mL.

51. The method of embodiment 36, wherein said first biocompatible organic solvent is present in said concentrated solution in an amount of from about 250 mg/mL to about 350 mg/mL.

52. The method of embodiment 36, wherein said second biocompatible organic solvent is present in said concentrated solution in an amount of from about 300 mg/mL to about 1 g/mL.

53. The method of embodiment 36, wherein said second biocompatible organic solvent is present in said concentrated solution in an amount of from about 400 mg/mL to about 900 mg/mL.

54. The method of embodiment 36, wherein said second biocompatible organic solvent is present in said concentrated solution in an amount of from about 600 mg/mL to about 700 mg/mL.

55. The method of embodiment 36, wherein said surfactant is present in said concentrated solution in an amount of from about 5 mg/mL to about 250 mg/mL.

56. The method of embodiment 36, wherein said surfactant is present in said concentrated solution in an amount of from about 10 mg/mL to about 150 mg/mL.

57. The method of embodiment 36, wherein said surfactant is present in said concentrated solution in an amount of from about 20 mg/mL to about 100 mg/mL.

58. The method of embodiment 36, wherein:
   a) said spicamycin derivative is present in said concentrated solution in an amount of from about 2 mg/mL to about 4 mg/mL;
   b) said first biocompatible organic solvent is present in said concentrated solution in an amount of from about 250 mg/mL to about 350 mg/mL;
   c) said second biocompatible organic solvent is present in said concentrated solution in an amount of from about 600 mg/mL to about 700 mg/mL; and
   d) said surfactant is present in said concentrated solution in an amount of from about 20 mg/mL to about 100 mg/mL.

59. The method of any one of embodiments 36-58, wherein said concentrated solution comprises:
   a) KRN5500 in an amount of about 4 mg/mL;
   b) ethanol in an amount of about 293 mg/mL;
   c) propylene glycol in an amount of about 618 mg/mL; and
   d) polysorbate 80 in an amount of about 40 mg/mL.

60. A method for preparing an intravenous solution, said method comprising contacting said concentrated solution of any one of embodiments 36-59 with an intravenous infusion liquid or diluent to produce an intravenous solution, wherein said intravenous solution is substantially free of particulates.

61. The method of embodiment 60, wherein said aqueous intravenous liquid or diluent is selected from the group consisting of:
   a) 0.9% sodium chloride;
   b) 5% dextrose; and
   c) Lactated Ringers solution.

62. The method of embodiment 60, wherein said concentrated solution is diluted into said intravenous infusion liquid or diluent at a ratio selected from the group consisting of:
   a) 1:10 (v/v);
   b) 1:30 (v/v); and
   c) 1:100 (v/v).

63. The method of embodiment 60, wherein:
   a) said spicamycin derivative is present in said intravenous solution in an amount of from about 0.01 mg/mL to about 0.03 mg/mL;
   b) said first biocompatible organic solvent is present in an amount of from about 2 mg/mL to about 3 mg/mL;
   c) said second biocompatible organic solvent is present in an amount of from about 4 mg/mL to about 7 mg/mL; and
   d) said surfactant is present in an amount of from about 0.2 mg/mL to about 0.5 mg/mL.

64. The method of embodiment 60, wherein said intravenous solution comprises:
   a) KRN5500 in an amount of about 0.04 mg/mL;
   b) ethanol in an amount of about 2.93 mg/mL;
   c) propylene glycol in an amount of about 6.18 mg/mL; and
   d) polysorbate 80 in an amount of about 0.40 mg/mL.

65. The method of embodiment 60, wherein said intravenous suspension further comprises a second analgesic or drug.

66. The method of embodiment 65, wherein said second analgesic or drug is an anti-inflammatory drug.

67. The method of any one of embodiments 36-66, wherein said first biocompatible organic solvent is selected from the group consisting of:
   a) ethanol; and
   b) t-butanol.

68. The method of embodiment 67, wherein said first biocompatible organic solvent is ethanol.

69. The method of any one of embodiments 36-68, wherein said second biocompatible organic solvent is selected from the group consisting of:
   a) propylene glycol;
   b) glycerin;

c) polyethylene glycol; and
d) polypropylene glycol.

70. The method of embodiment 69, wherein said second biocompatible organic solvent is propylene glycol.

71. The method of any one of embodiments 36-70, wherein said surfactant is selected from the group consisting of:
   a) polysorbate;
   b) a poloxamer;
   c) n-dodecyl-b-maltoside;
   d) tocopheryl-polyethylene glycol succinate;
   e) polyethylene glycol;
   f) a polyoxyl;
   g) Solutol;
   h) Pluronics;
   i) sodium dodecyl sulfate;
   j) SPAN, and
   k) octoxynol-9.

72. The method of embodiment 71, wherein said surfactant is polysorbate.

73. A method for treating or preventing pain in a subject, said method comprising administering to a subject in need thereof a treatment or prevention effective amount of the composition of any one of embodiments 1-35.

74. The method of embodiment 73, wherein said pain is neuropathic pain.

75. The method of embodiment 74, wherein said neuropathic pain is due to a neuropathy selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post-surgical pain syndrome, post mastectomy syndrome, post thoracotomy syndrome, phantom pain, nerve root avulsion, post radiation neuropathy, repetitive movement nerve injury, repetitive stress injury, and post injury neuropathy.

76. The method of embodiment 75, wherein said chemotherapy-induced neuropathy is chemotherapy-induced peripheral neuropathy.

77. The method of embodiment 76, wherein said chemotherapy-induced peripheral neuropathy is painful chemotherapy-induced peripheral neuropathy.

78. The method of embodiment 77, wherein said painful chemotherapy-induced peripheral neuropathy is painful acute chemotherapy-induced peripheral neuropathy.

79. The method of embodiment 77, wherein said painful chemotherapy-induced peripheral neuropathy is painful chronic chemotherapy-induced peripheral neuropathy.

80. The method of embodiment 73, wherein said composition is administered in a combination formulation comprising said composition and a second analgesic or drug.

81. The method of embodiment 80, wherein said second analgesic or drug is an anti-inflammatory drug.

The present invention is explained in greater detail in the following non-limiting Examples.

EXAMPLES

The following compositions were formulated using combinations of the spicamycin derivative KRN5500 with ethanol (i.e., a first biocompatible organic solvent), propylene glycol (i.e., a second biocompatible organic solvent), and a surfactant. The concentration of the spicamycin derivative KRN5500 in a concentrated solution was determined by high performance liquid chromatography (HPLC). The properties of the concentrated solutions and in diluted intravenous solutions were also determined at the time of formulation and at various time points following storage at different temperatures. It would be known to those of ordinary skill in the art that clear solutions with the presence of very few particles in suspension would be in accordance with the regulations established by the U.S. Pharmaceutical Convention in General Chapter <788> Particulate Matter in Injections and the USP Particle Count Reference Standard, as described above, and would be suitable for administration to a subject.

Formulation F4:
Active pharmaceutical ingredient (API) KRN5500: theoretical concentration 0.116 mg/ml, ethanol 30% w/v and propylene glycol 70% w/v.

Ethanol (96%) was added to KRN5500. The appearance of the solution after 50 minutes of stirring was clear without precipitate. The solution was then brought to final volume with propylene glycol. The solution remained clear and then was filtered with PVDF 0.22 µm. The solution was then divided into two aliquots. The first aliquot was stored in at 2-8° C. while the second aliquot was stored at 40° C. After 24 hours, the solutions remained clear. An aliquot of the solution was analyzed by HPLC and the assay was 0.21 mg/mL. The solution was then diluted with 0.9% sodium chloride or 5% Dextrose. Initially, in both diluted solutions, there were free particles and after 2 hours there was an increase in the precipitate.

Formulation 4c:
Active pharmaceutical ingredient (API) KRN5500: theoretical concentration 1.012 mg/ml, ethanol 30% w/v, Tween 10% w/v and propylene glycol 60% w/v.

Ethanol (96%) (7.82 g) was added to KRN5500. The appearance of the solution after 45 minutes of stirring was opalescent with precipitate. To the solution was added 2.504 g of Tween 80 but it remained opalescent. The solution was then brought to final volume with 15 g of propylene glycol. The solution became clear with some particles and then was filtrated with PVDF 0.22 µm. The density of the final solution was 0.961 g/mL and the pH was 6.3. The solution was divided into two aliquots. The first aliquot was stored in at 2-8° C. while the second aliquot was stored at 25° C. The solution was analyzed by HPLC. The solution was then diluted with 0.9% sodium chloride, 5% Dextrose or Lactated Ringers solution in different ratios. The properties of the solutions are shown in Table 2 below.

TABLE 2

|  | Theoretical concentration (mg/mL) | HPLC assay (mg/mL) | pH | Appearance t = 0 | Appearance t = 24 h RT | Appearance t = 24 h T = 2-8° C. | Appearance t = 48 h RT | Appearance t = 48 h T = 2-8° C. |
|---|---|---|---|---|---|---|---|---|
| Formulation 4c | 1.012 | 0.982 | 6.30 | Clear solution | Clear solution | Clear solution | Clear solution | Clear solution |
| Formulation 4c 1:10 NaCl 0.9% | 0.101 | 0.095 | 6.20 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |

TABLE 2-continued

| | Theoretical concentration (mg/mL) | HPLC assay (mg/mL) | pH | Appearance t = 0 | Appearance t = 24 h RT | Appearance t = 24 h T = 2-8° C. | Appearance t = 48 h RT | Appearance t = 48 h T = 2-8° C. |
|---|---|---|---|---|---|---|---|---|
| Formulation 4c 1:30 NaCl 0.9% | 0.034 | 0.035 | 6.00 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:100 NaCl 0.9% | 0.010 | 0.010 | 5.11 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:10 Dextrose 5% | 0.101 | 0.104 | 6.60 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:30 Dextrose 5% | 0.034 | 0.033 | 6.50 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:100 Dextrose 5% | 0.010 | 0.011 | 6.21 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:10 RL | 0.101 | 0.104 | 6.04 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:30 RL | 0.034 | 0.030 | 5.96 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4c 1:100 RL | 0.010 | 0.011 | 5.89 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |

The addition of Tween 80 avoided the precipitation of KRN5500 after dilution. The recovery for these solutions was only slightly less than 100% except for Formulation 4c 1:10 in 0.9% sodium chloride and Formulation 4c 1:100 in Lactated Ringers solution.

Formulation F4c was then kept under stability for up to 2 weeks at 2-8° C. After 2 weeks a slight increase of the number of particles was observed in the solutions. The properties of the solutions prepared from this solution are shown in Table 3 below.

TABLE 3

| | Theoretical concentration (mg/mL) | HPLC assay (mg/mL) | pH | Appearance t = 0 | Appearance t = 24 h RT | Appearance t = 24 h T = 2-8° C. | Appearance t = 48 h RT | Appearance t = 48 h T = 2-8° C. | Appearance t = 2 weeks T = 2-8° C. |
|---|---|---|---|---|---|---|---|---|---|
| Formulation 4c | 1.012 | 0.982 | 6.30 | Clear solution | Clear solution | Clear solution | Clear solution | Clear solution | Clear solution |
| Formulation 4c 1:10 NaCl 0.9% | 0.101 | 0.095 | 6.20 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:30 NaCl 0.9% | 0.034 | 0.035 | 6.00 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:100 NaCl 0.9% | 0.010 | 0.010 | 5.11 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |

TABLE 3-continued

| | Theoretical concentration (mg/mL) | HPLC assay (mg/mL) | pH | Appearance t = 0 | Appearance t = 24 h RT | Appearance t = 24 h T = 2-8° C. | Appearance t = 48 h RT | Appearance t = 48 h T = 2-8° C. | Appearance t = 2 weeks T = 2-8° C. |
|---|---|---|---|---|---|---|---|---|---|
| Formulation 4c 1:10 Dextrose 5% | 0.101 | 0.104 | 6.60 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:30 Dextrose 5% | 0.034 | 0.033 | 6.50 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:100 Dextrose 5% | 0.010 | 0.011 | 6.21 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:10 RL | 0.101 | 0.104 | 6.04 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:30 RL | 0.034 | 0.030 | 5.96 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |
| Formulation 4c 1:100 RL | 0.010 | 0.011 | 5.89 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension | Clear solution with presence of some particles in suspension |

Formulation F4e

Active pharmaceutical ingredient (API) KRN5500: theoretical concentration 1.019 mg/ml, ethanol 30% w/v, Tween 5% w/v and propylene glycol 65% w/v.

Ethanol (96%) (7.82 g) was added to KRN5500 along with 1.25 g of Tween 80. The appearance of the solution after 65 minutes of stirring was opalescent with precipitate. The solution was then brought to final volume with 16.25 g of propylene glycol. After 30 minutes of stirring the solution was clear and was filtered with PVDF 0.22 μm. The density of the final solution was 0.955 g/mL and the pH was 6.3. The solution was divided into two aliquots. The first aliquot was stored in at 2-8° C. while the second aliquot was stored at 25° C. Another aliquot was analyzed by HPLC. The solution was then diluted with 0.9% sodium chloride, 5% Dextrose or Lactated Ringers solution in different ratios. The properties of the solutions are shown in Table 4 below.

TABLE 4

| | Theoretical concentration (mg/mL) | HPLC assay (mg/mL) | pH | Appearance t = 0 | Appearance t = 24 h RT | Appearance t = 24 h T = 2-8° C. | Appearance t = 48 h RT | Appearance t = 48 h T = 2-8° C. |
|---|---|---|---|---|---|---|---|---|
| Formulation 4e | 1.019 | NA | 6.30 | Clear solution | Clear solution | Clear solution | Clear solution | Clear solution |
| Formulation 4e 1:10 NaCl 0.9% | 0.102 | NA | 5.20 | Slightly opalescent solution with presence of very few particles in suspension | Slightly opalescent solution with presence of very few particles in suspension | Slightly opalescent solution with presence of very few particles in suspension | Slightly opalescent solution with presence of very few particles in suspension | Slightly opalescent solution with presence of very few particles in suspension |
| Formulation 4e 1:30 NaCl 0.9% | 0.034 | NA | 7.00 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4e 1:100 NaCl 0.9% | 0.0102 | NA | 5.60 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |

TABLE 4-continued

|  | Theoretical concentration (mg/mL) | HPLC assay (mg/mL) | pH | Appearance t = 0 | Appearance t = 24 h RT | Appearance t = 24 h T = 2-8° C. | Appearance t = 48 h RT | Appearance t = 48 h T = 2-8° C. |
|---|---|---|---|---|---|---|---|---|
| Formulation 4e 1:10 Dextrose 5% | 0.102 | NA | 5.60 | Slightly opalescent solution with presence of very few particles in suspension | Slightly opalescent solution with presence of very few particles in suspension | Slightly opalescent solution with presence of very few particles in suspension | Slightly opalescent solution with presence of very few particles in suspension | Slightly opalescent solution with presence of very few particles in suspension |
| Formulation 4e 1:30 Dextrose 5% | 0.034 | NA | 7.00 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4e 1:100 Dextrose 5% | 0.0102 | NA | 6.40 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4e 1:10 RL | 0.102 | NA | 6.00 | Slightly opalescent solution with presence of very few particles in suspension | Slightly opalescent solution with presence of very few particles in suspension | Slightly opalescent solution with presence of very few particles in suspension | Slightly opalescent solution with presence of very few particles in suspension | Slightly opalescent solution with presence of very few particles in suspension |
| Formulation 4e 1:30 RL | 0.034 | NA | 6.00 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4e 1:100 RL | 0.0102 | NA | 5.90 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |

Formulation F4f

Active pharmaceutical ingredient (API) KRN5500: theoretical concentration 1.019 mg/ml, ethanol 30% w/v, Tween 2% w/v and propylene glycol 68% w/v.

Ethanol (96%) (7.81 g) was added to KRN5500 along with 0.499 g of Tween 80. The appearance of the solution after 65 minutes of stirring was opalescent with precipitate. The solution was then brought to final volume with 16.99 g of propylene glycol. After 35 minutes of stirring the solution was clear and was filtered with PVDF 0.22 μm. The density of the final solution was 0.954 g/mL and the pH was 6.4. The solution was divided into two aliquots. The first aliquot was stored in at 2-8° C. while the second aliquot was stored at 25° C. Another aliquot was analyzed by HPLC. The solution was then diluted with 0.9% sodium chloride, 5% Dextrose or Lactated Ringers solution in different ratios. The properties of the solutions are shown in Table 5 below.

TABLE 5

|  | Theoretical concentration (mg/mL) | pH | Appearance t = 0 | Appearance t = 24 h RT | Appearance t = 24 h T = 2-8° C. | Appearance t = 48 h RT | Appearance t = 48 h T = 2-8° C. |
|---|---|---|---|---|---|---|---|
| Formulation 4f | 0.995 | 6.40 | Clear solution | Clear solution | Clear solution | Clear solution | Clear solution |
| Formulation 4f 1:10 NaCl 0.9% | 0.0995 | 5.60 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4f 1:30 NaCl 0.9% | 0.0332 | 7.10 | Clear solution with presence of few particles in suspension | Clear solution with presence of few particles in suspension | Clear solution with presence of few particles in suspension | Clear solution with presence of few particles in suspension | Clear solution with presence of few particles in suspension |
| Formulation 4f 1:100 NaCl 0.9% | 0.00995 | 5.80 | Clear solution with presence of few particles in suspension | Clear solution with presence of few particles in suspension | Clear solution with presence of few particles in suspension | Clear solution with presence of few particles in suspension | Clear solution with presence of few particles in suspension |

TABLE 5-continued

| | Theoretical concentration (mg/mL) | pH | Appearance t = 0 | Appearance t = 24 h RT | Appearance t = 24 h T = 2-8° C. | Appearance t = 48 h RT | Appearance t = 48 h T = 2-8° C. |
|---|---|---|---|---|---|---|---|
| Formulation 4f 1:10 Dextrose 5% | 0.0995 | 6.30 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4f 1:30 Dextrose 5% | 0.0332 | 6.90 | Clear solution with presence of few particles in suspension | Clear solution with presence of few particles in suspension | Clear solution with presence of few particles in suspension | Clear solution with presence of few particles in suspension | Clear solution with presence of few particles in suspension |
| Formulation 4f 1:100 Dextrose 5% | 0.00995 | 6.40 | Clear solution with presence of few particles in suspension | Clear solution with presence of few particles in suspension | Clear solution with presence of few particles in suspension | Clear solution with presence of few particles in suspension | Clear solution with presence of few particles in suspension |
| Formulation 4f 1:10 RL | 0.0995 | 6.00 | Clear solution with presence of very few particles in suspension | Clear solution with presence of very few particles in suspension | Clear solution with presence of very few particles in suspension | Clear solution with presence of very few particles in suspension | Clear solution with presence of very few particles in suspension |
| Formulation 4f 1:30 RL | 0.0332 | 7.20 | Clear solution with presence of few particles in suspension | Clear solution with presence of few particles in suspension | Clear solution with presence of few particles in suspension | Clear solution with presence of few particles in suspension | Clear solution with presence of few particles in suspension |
| Formulation 4f 1:100 RL | 0.00995 | 5.90 | Clear solution with presence of few particles in suspension | Clear solution with presence of few particles in suspension | Clear solution with presence of few particles in suspension | Clear solution with presence of few particles in suspension | Clear solution with presence of few particles in suspension |

Formulation F4e 2 mg/mL
Active pharmaceutical ingredient (API) KRN5500: theoretical concentration 1.923 mg/ml, ethanol 30% w/v, Tween 5% w/v and propylene glycol 65% w/v.
Ethanol (96%) (7.81 g) was added to KRN5500 along with 1.259 g of Tween 80. The appearance of the solution was opalescent with precipitate. The solution was then brought to final volume with 16.25 g of propylene glycol. After 30 minutes of stirring the solution was clear and was filtered with PVDF 0.22 μm. The density of the final solution was 0.953 g/mL and the pH was 6.6. The solution was divided into two aliquots. The first aliquot was stored in at 2-8° C. while the second aliquot was stored at 25° C. Another aliquot was analyzed by HPLC. The solution was then diluted with 0.9% sodium chloride, 5% Dextrose or Lactated Ringers solution in different ratios. The properties of the solutions are shown in Table 6 below.

TABLE 6

| F4e 2 mg/mL | Theoretical concentration (mg/mL) | HPLC assay (mg/mL) | pH | Appearance t = 0 | Appearance t = 24 h RT | Appearance t = 24 h T = 2-8° C. | Appearance t = 96 h RT | Appearance t = 96 h T = 2-8° C. |
|---|---|---|---|---|---|---|---|---|
| Formulation 4e | 1.923 | NA | 6.6 | Clear solution | Clear solution | Clear solution | Clear solution | Clear solution |
| Formulation 4e 1:10 NaCl 0.9% | 0.1923 | NA | 7.20 | Slightly opalescent solution with presence of very few particles in suspension | Slightly opalescent solution with presence of very few particles in suspension | Slightly opalescent solution with presence of very few particles in suspension | Slightly opalescent solution with presence of few particles in suspension | Slightly opalescent solution with presence of few particles in suspension |
| Formulation 4e 1:30 NaCl 0.9% | 0.0641 | NA | 6.40 | Clear solution with presence of very few particles in suspension | Clear solution with presence of few particles in suspension | Clear solution with presence of few particles in suspension | Clear solution with presence of some particles in suspension | Clear solution with presence of some particles in suspension |
| Formulation 4e 1:100 NaCl 0.9% | 0.0192 | NA | 6.60 | Clear solution with presence of very few particles in suspension | Clear solution with presence of few particles in suspension | Clear solution with presence of few particles in suspension | Clear solution with presence of some particles in suspension | Clear solution with presence of some particles in suspension |

TABLE 6-continued

| F4e 2 mg/mL | Theoretical concentration (mg/mL) | HPLC assay (mg/mL) | pH | Appearance t = 0 | Appearance t = 24 h RT | Appearance t = 24 h T = 2-8° C. | Appearance t = 96 h RT | Appearance t = 96 h T = 2-8° C. |
|---|---|---|---|---|---|---|---|---|
| Formulation 4e 1:10 Dextrose 5% | 0.1923 | NA | 7.40 | Slightly opalescent solution with presence of very few particles in suspension | Slightly opalescent solution with presence of very few particles in suspension | Slightly opalescent solution with presence of very few particles in suspension | Slightly opalescent solution with presence of few particles in suspension | Slightly opalescent solution with presence of few particles in suspension |
| Formulation 4e 1:30 Dextrose 5% | 0.0641 | NA | 6.70 | Clear solution with presence of very few particles in suspension | Clear solution with presence of few particles in suspension | Clear solution with presence of few particles in suspension | Clear solution with presence of some particles in suspension | Clear solution with presence of some particles in suspension |
| Formulation 4e 1:100 Dextrose 5% | 0.0192 | NA | 6.60 | Clear solution with presence of very few particles in suspension | Clear solution with presence of few particles in suspension | Clear solution with presence of few particles in suspension | Clear solution with presence of some particles in suspension | Clear solution with presence of some particles in suspension |
| Formulation 4e 1:10 RL | 0.1923 | NA | 6.30 | Slightly opalescent solution with presence of very few particles in suspension | Slightly opalescent solution with presence of very few particles in suspension | Slightly opalescent solution with presence of very few particles in suspension | Slightly opalescent solution with presence of few particles in suspension | Slightly opalescent solution with presence of few particles in suspension |
| Formulation 4e 1:30 RL | 0.0641 | NA | 6.00 | Clear solution with presence of very few particles in suspension | Clear solution with presence of few particles in suspension | Clear solution with presence of few particles in suspension | Clear solution with presence of some particles in suspension | Clear solution with presence of some particles in suspension |
| Formulation 4e 1:100 RL | 0.0192 | NA | 6.00 | Clear solution with presence of very few particles in suspension | Clear solution with presence of few particles in suspension | Clear solution with presence of few particles in suspension | Clear solution with presence of some particles in suspension | Clear solution with presence of some particles in suspension |

Formulation F4f 2 mg/mL:
Active pharmaceutical ingredient (API) KRN5500: theoretical concentration 1.826 mg/ml, ethanol 30% w/v, Tween 2% w/v and propylene glycol 68% w/v.
Ethanol (96%) (7.81 g) was added to KRN5500 along with 0.499 g of Tween 80. The appearance of the solution after 65 minutes of stirring was opalescent with precipitate. The solution was then brought to final volume with 17.00 g of propylene glycol. After 35 minutes of stirring the solution was clear and was filtered with PVDF 0.22 μm. The density of the final solution was 0.952 g/mL and the pH was 6.0.

The solution was divided into two aliquots. The first aliquot was stored in at 2-8° C. while the second aliquot was stored at 25° C. Another aliquot was analyzed by HPLC. The solution was then diluted with 0.9% sodium chloride, 5% Dextrose or Lactated Ringers solution in different ratios. The properties of the solutions are shown in Table 7 below.

TABLE 7

| F4f 2 mg/mL | Theoretical concentration (mg/mL) | HPLC assay (mg/mL) | pH | Appearance t = 0 | Appearance t = 24 h RT | Appearance t = 24 h T = 2-8° C. | Appearance t = 96 h RT | Appearance t = 96 h T = 2-8° C. |
|---|---|---|---|---|---|---|---|---|
| Formulation 4f | 1.826 | NA | 6.00 | Clear solution | Clear solution | Clear solution | Clear solution | Clear solution |
| Formulation 4f 1:10 NaCl 0.9% | 0.1826 | NA | 7.00 | Clear solution with presence of very few particles in suspension | Clear solution with presence of very few particles in suspension | Clear solution with presence of very few particles in suspension | Clear solution with presence of few particles in suspension | Clear solution with presence of few particles in suspension |
| Formulation 4f 1:30 NaCl 0.9% | 0.0609 | NA | 6.70 | Clear solution with presence of few particles in suspension | Clear solution with presence of few particles in suspension | Clear solution with presence of few particles in suspension | Clear solution with presence of some particles in suspension | Clear solution with presence of some particles in suspension |
| Formulation 4f 1:100 NaCl 0.9% | 0.0183 | NA | 7.00 | Clear solution with presence of few particles in suspension | Clear solution with presence of few particles in suspension | Clear solution with presence of few particles in suspension | Clear solution with presence of some particles in suspension | Clear solution with presence of some particles in suspension |

TABLE 7-continued

| F4f 2 mg/mL | Theoretical concentration (mg/mL) | HPLC assay (mg/mL) | pH | Appearance t = 0 | Appearance t = 24 h RT | Appearance t = 24 h T = 2-8° C. | Appearance t = 96 h RT | Appearance t = 96 h T = 2-8° C. |
|---|---|---|---|---|---|---|---|---|
| Formulation 4f 1:10 Dextrose 5% | 0.1826 | NA | 6.90 | Clear solution with presence of very few particles in suspension | Clear solution with presence of very few particles in suspension | Clear solution with presence of very few particles in suspension | Clear solution with presence of few particles in suspension | Clear solution with presence of few particles in suspension |
| Formulation 4f 1:30 Dextrose 5% | 0.0609 | NA | 6.80 | Clear solution with presence of few particles in suspension | Clear solution with presence of few particles in suspension | Clear solution with presence of few particles in suspension | Clear solution with presence of some particles in suspension | Clear solution with presence of some particles in suspension |
| Formulation 4f 1:100 Dextrose 5% | 0.0183 | NA | 6.80 | Clear solution with presence of few particles in suspension | Clear solution with presence of few particles in suspension | Clear solution with presence of few particles in suspension | Clear solution with presence of some particles in suspension | Clear solution with presence of some particles in suspension |
| Formulation 4f 1:10 RL | 0.1826 | NA | 6.20 | Clear solution with presence of very few particles in suspension | Clear solution with presence of very few particles in suspension | Clear solution with presence of very few particles in suspension | Clear solution with presence of few particles in suspension | Clear solution with presence of few particles in suspension |
| Formulation 4f 1:30 RL | 0.0609 | NA | 6.00 | Clear solution with presence of few particles in suspension | Clear solution with presence of few particles in suspension | Clear solution with presence of few particles in suspension | Clear solution with presence of some particles in suspension | Clear solution with presence of some particles in suspension |
| Formulation 4f 1:100 RL | 0.0183 | NA | 6.00 | Clear solution with presence of few particles in suspension | Clear solution with presence of few particles in suspension | Clear solution with presence of few particles in suspension | Clear solution with presence of some particles in suspension | Clear solution with presence of some particles in suspension |

Formulation 01 2 mg/mL

Active pharmaceutical ingredient (API) KRN5500: concentration 2.0 mg/mL, ethanol 293.33 mg/mL, Lutrol F68 10 mg/mL, and propylene glycol 650.0 mg/mL. Formulation 01 was prepared according to the process outlined in FIG. 1. Briefly, 3.00 g of Lutrol F68 was added to 88.00 g of ethanol (96%) and mixed for 6 minutes until the Lutrol F68 was completely dissolved. KRN5500 (theoretical weight of 600 mg) was then slowly added and the solution was stirred for 17 minutes. Propylene glycol (195.0 g) was then added and the solution was stirred for 46 minutes until complete dissolution of the KRN5500. Prior to filtration, the solution was clear and colorless. Following filtration through a 0.2 μm nylon membrane, the solution remained clear and colorless and had a density of 0.954 g/mL. The formulation was prepared in a lot of 300 mL for packaging in 5 mL vials using the amounts of each component/excipient in Table 8 below.

TABLE 8

| Component/Excipient | Quantity/mL | Quantity/vial | Quantity/lot |
|---|---|---|---|
| KRN5500 (API) | 2.00 mg | 10.00 mg | 600 mg |
| Lutrol F68 | 10.00 mg | 50.00 mg | 3.00 g |
| Propylene glycol | 650.00 mg | 3.25 g | 195.00 g |
| Ethanol 96% | 293.33 mg | 1.47 g | 88.00 g |

Formulation 02 2 mg/mL

Figure 2:
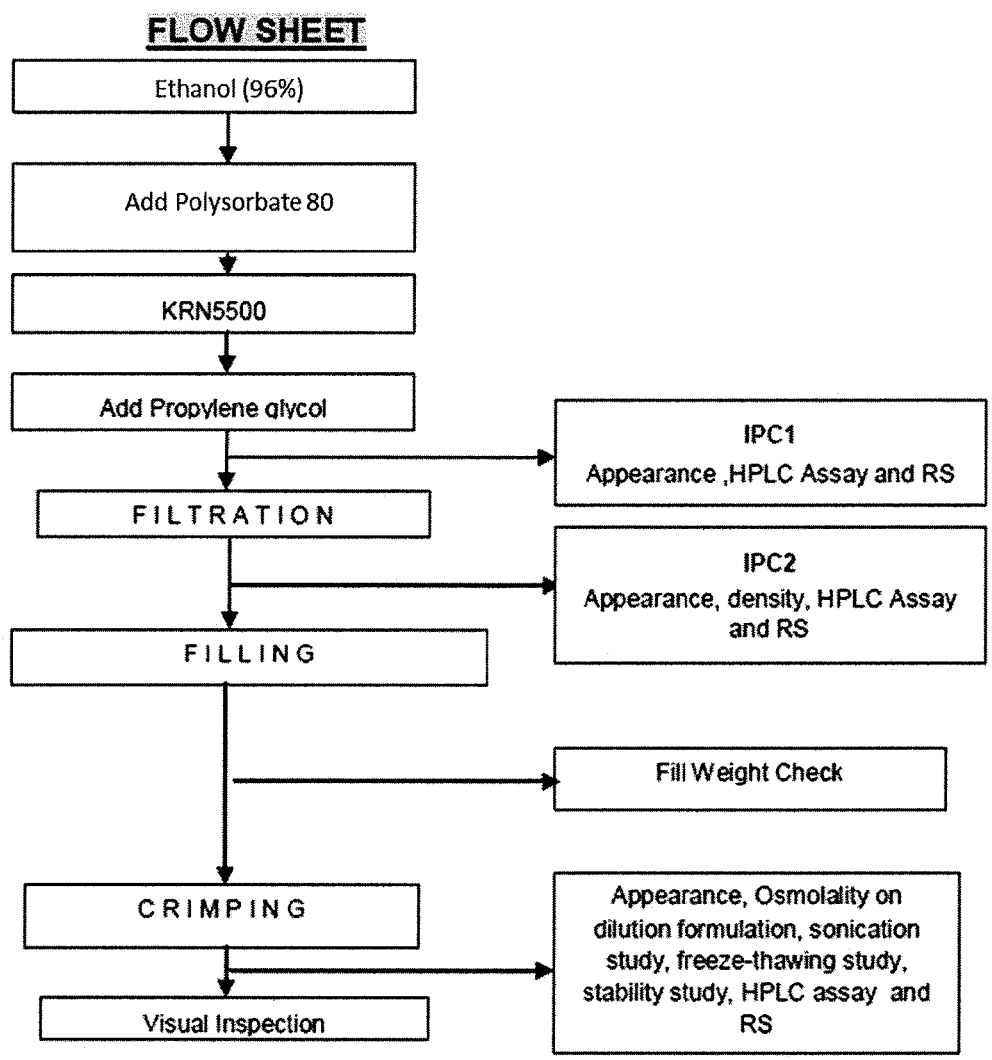
FIG. 2 shows a manufacturing process flow chart for the production of a composition of the invention, wherein the surfactant is polysorbate 80.

Active pharmaceutical ingredient (API) KRN5500: concentration 2.0 mg/mL, ethanol 293.33 mg/mL, polysorbate 80 20.00 mg/mL, and propylene glycol 640.0 mg/mL. Formulation 02 was prepared according to the process outlined in FIG. 2. Briefly, 6.00 g of polysorbate 80 was added to 88.00 g of ethanol (96%) and mixed for 8 minutes until the polysorbate 80 was completely dissolved. KRN5500 (theoretical weight of 600 mg) was then slowly added and the solution was stirred for 21 minutes. Propylene glycol (192.0 g) was then added and the solution was stirred for 45 minutes until complete dissolution of the KRN5500. Prior to filtration, the solution was clear and colorless. Following filtration through a 0.2 μm nylon membrane, the solution remained clear and colorless and had a density of 0.955 g/mL. The formulation was prepared in a lot of 300 mL for packaging in 5 mL vials using the amounts of each component/excipient in Table 9 below.

TABLE 9

| Component/Excipient | Quantity/mL | Quantity/vial | Quantity/lot |
|---|---|---|---|
| KRN5500 (API) | 2.00 mg | 10.00 mg | 600 mg |
| Polysorbate 80 | 20.00 mg | 100.00 mg | 6.00 g |
| Propylene glycol | 840.00 mg | 3.20 g | 192.00 g |
| Ethanol 96% | 293.33 mg | 1.47 g | 88.00 g |

Formulation 03 4 mg/mL

Active pharmaceutical ingredient (API) KRN5500: concentration 4.0 mg/mL, ethanol 293.30 mg/mL, polysorbate 80 40.00 mg/mL, and propylene glycol 617.75 mg/mL. Formulation 03 was prepared according to the process outlined in FIG. 2. Briefly, 8.00 g of polysorbate 80 was added to 58.66 g of ethanol (96%) and mixed for 10 minutes until the polysorbate 80 was completely dissolved. KRN5500 (theoretical weight of 800 mg) was then slowly added and the solution was stirred for 15 minutes. Propylene glycol (123.55 g) was then added and the solution was stirred for 48 minutes until complete dissolution of the KRN5500. Prior to filtration, the solution was clear and colorless. Following filtration through a 0.2 µm nylon membrane, the solution remained clear and colorless and had a density of 0.955 g/mL. The formulation was prepared in a lot of 200 mL for packaging in 2.5 mL vials using the amounts of each component/excipient in Table 10 below.

TABLE 10

| Component/Excipient | Quantity/mL | Quantity/vial | Quantity/lot |
|---|---|---|---|
| KRN5500 (API) | 4.00 mg | 10.00 mg | 800 mg |
| Polysorbate 80 | 40.00 mg | 100.00 mg | 8.00 g |
| Propylene glycol | 617.75 mg | 1.54 g | 123.55 g |
| Ethanol 96% | 293.30 mg | 733.25 mg | 58.66 g |

Stability Studies of Formulations 01, 02, and 03

Stability studies were performed with formulations 01, 02, and 03 when prepared in vials and stored at 5° C., 25° C. and 40° C. Table 11 and Table 12 indicate the total related substance (TRS) levels and anomer levels for each of the formulations, respectively.

TABLE 11

| | | Total Related Substances (%) | | | | |
|---|---|---|---|---|---|---|
| Formulation | Initial | 2 weeks @40° C. | 1 month @40° C. | 1 month @25° C. | 2 months @25° C. | 3 months @25° C. |
| 01 | 0.53 | 2.1 | 5.15 | 1.32 | 1.72 | 1.97 |
| 02 | 0.50 | 1.4 | 3.07 | 1.04 | 1.07 | 1.26 |
| 03 | 0.54 | 1.4 | 2.60 | 1.02 | 0.92 | 1.20 |

TABLE 12

| | | Anomer level, RRT ~0.90 (%) | | | | |
|---|---|---|---|---|---|---|
| Formulation | Initial | 2 weeks @40° C. | 1 month @40° C. | 1 month @25° C. | 2 months @25° C. | 3 months @25° C. |
| 01 | 0.05 | 1.10 | 3.10 | 0.35 | 0.61 | 0.89 |
| 02 | 0.05 | 0.72 | 1.68 | 0.23 | 0.37 | 0.52 |
| 03 | 0.05 | 0.66 | 1.60 | 0.24 | 0.37 | 0.51 |

In-Use Dosing Solution Stability Study

Table 13 indicates the TRS levels when formulations 01, 02, and 03 were diluted into 0.9% NaCl and stored at 5° C. and 25° C. for 24 hours.

TABLE 13

| | Total Related Substances (%) | | | | | |
|---|---|---|---|---|---|---|
| | 01 | | 02 | | 03 | |
| Dilution in 0.9% NaCl | 0.01 mg/mL KRN5500 | 0.1 mg/mL KRN5500 | 0.01 mg/mL KRN5500 | 0.1 mg/mL KRN5500 | 0.01 mg/mL KRN5500 | 0.1 mg/mL KRN5500 |
| Initial | 0.45 | 0.40 | 0.44 | 0.44 | 0.40 | 0.47 |
| 24 hours @ 5° C. | 0.52 | 0.46 | 0.39 | 0.48 | 0.43 | 0.49 |
| 24 hours @ 25° C. | 0.78 | 0.52 | 0.70 | 0.55 | 0.64 | 0.48 |

Osmolality Study

Table 14 indicates the osmolality when formulations 01, 02, and 03 were diluted into 0.9% NaCl, 5% Dextrose, or Lactated Ringers.

TABLE 14

| | Osmolality (mOsmol/hg) | | | | | |
|---|---|---|---|---|---|---|
| | 01 | | 02 | | 03 | |
| Dilution Vehicle | 0.01 mg/mL KRN5500 | 0.1 mg/mL KRN5500 | 0.01 mg/mL KRN5500 | 0.1 mg/mL KRN5500 | 0.01 mg/mL KRN5500 | 0.1 mg/mL KRN5500 |
| Lactated Ringers | 324 | 1022 | 317 | 949 | 289 | 826 |
| 0.9%NaCl | 360 | 995 | 369 | 1016 | 327 | 903 |

TABLE 14-continued

| | Osmolality (mOsmol/hg) | | | | | |
|---|---|---|---|---|---|---|
| | 01 | | 02 | | 03 | |
| Dilution Vehicle | 0.01 mg/mL KRN5500 | 0.1 mg/mL KRN5500 | 0.01 mg/mL KRN5500 | 0.1 mg/mL KRN5500 | 0.01 mg/mL KRN5500 | 0.1 mg/mL KRN5500 |
| 5.0% Dextrose | 346 | 1035 | 340 | 1025 | 315 | 632 |

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

That which is claimed:

1. A composition comprising:
   a) a spicamycin derivative of Formula II:

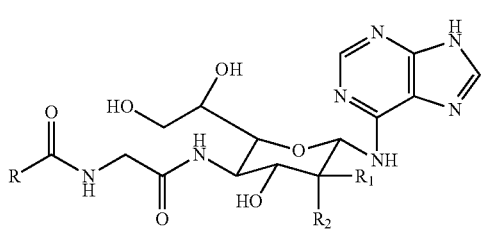

wherein $R_1$ and $R_2$ are different from each other and represent H or OH, and R represents a substituted or unsubstituted alkyl, alkenyl, alkynyl, or cycloalkyl;
   b) a biocompatible alcohol that solubilizes said spicamycin derivative;
   c) glycerin or a glycol that is miscible with said biocompatible alcohol and solubilizes said spicamycin derivative; and
   d) a surfactant soluble in a mixture of said biocompatible alcohol and said glycerin or glycol;
   wherein said composition is essentially free of mono-ethanolamine, and wherein said composition is a single-phase solution.

2. The composition of claim 1, further comprising an aqueous intravenous liquid or diluent.

3. The composition of claim 2, wherein said aqueous intravenous liquid or diluent is selected from the group consisting of:
   a) 0.9% sodium chloride;
   b) 5% dextrose; and
   c) Lactated Ringers solution.

4. The composition of claim 1, wherein said composition is substantially free of particulates.

5. The composition of claim 1, wherein said composition is substantially free of particulates for about two weeks after said composition is formulated.

6. The composition of claim 1, wherein said composition is substantially free of particulates for at least 1 year after said composition is formulated.

7. The composition of claim 1, wherein said composition is essentially free of N,N-dimethyl acetamide (DMAC).

8. The composition of claim 1, wherein said spicamycin derivative is a compound of Formula II and R is selected from the group consisting of:
   a) a linear alkenyl having 11-13 carbon atoms;
   b) a linear, unsubstituted alkyl having 11-13 carbon atoms and no double or triple bonds;
   c) a linear haloalkyl having 10-15 carbon atoms;
   d) $CH_3(CH_2)_nCH(OH)$— or $CH_3(CH_2)_{n-1}CH(OH)CH_2$—, wherein n denotes an integer from 9-13;
   e) an alkyl having 10-15 carbon atoms substituted with an azide group or a cyano group;
   f) a linear alkyl having 10-13 carbon atoms substituted with a phenoxy group or a halogen-substituted phenoxy group;

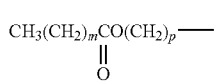

wherein m denotes an integer from 0-2 and p denotes an integer from 9-14;

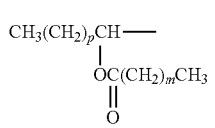

wherein m denotes an integer from 0-2 and p denotes an integer from 8-13;

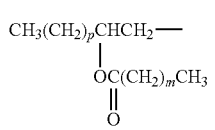

wherein m denotes an integer from 0-2 and p denotes an integer from 10-15;
   j) $CH_3(CH_2)_mSO_2O(CH_2)_p$—, wherein m denotes an integer from 0-3 and p denotes an integer from 9-14;

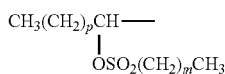

k)

wherein m denotes an integer from 0-3 and p denotes an integer from 10-15;

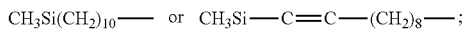

l)

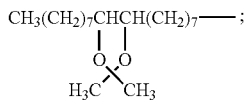

m)

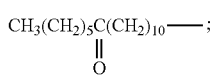

n)

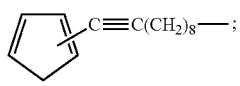

o)

and p) a linear alkadienyl having 11-13 carbon atoms.

9. The composition of claim 8, wherein $R_1$ is H and $R_2$ is OH.

10. The composition of claim 8, wherein said spicamycin derivative is 6-[4-deoxy-4-[(2E,4E)-tetradecadienoylglycyl]amino-L-glycero-β-L-manno heptopyranosyl]amino-9H-purine (KRN5500) and has the following structure:

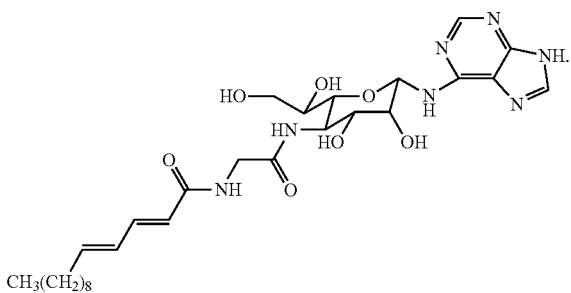

11. The composition of claim 1, wherein said spicamycin derivative is present in an amount of from about 0.01 mg/mL to about 10 mg/mL.

12. The composition of claim 1, wherein said spicamycin derivative is present in an amount of from about 0.1 mg/mL to about 5 mg/mL.

13. The composition of claim 1, wherein said spicamycin derivative is present in an amount of from about 2 mg/mL to about 4 mg/mL.

14. The composition of claim 1, wherein said biocompatible alcohol is present in an amount of from about 1 mg/mL to about 500 mg/mL.

15. The composition of claim 1, wherein said biocompatible alcohol is present in an amount of from about 100 mg/mL to about 450 mg/mL.

16. The composition of claim 1, wherein said biocompatible alcohol is present in an amount of from about 250 mg/mL to about 350 mg/mL.

17. The composition of claim 1, wherein said glycerin or glycol is present in an amount of from about 1 mg/mL to about 1 g/mL.

18. The composition of claim 1, wherein said glycerin or glycol is present in an amount of from about 300 mg/mL to about 900 mg/mL.

19. The composition of claim 1, wherein said glycerin or glycol is present in an amount of from about 600 mg/mL to about 700 mg/mL.

20. The composition of claim 1, wherein said surfactant is present in an amount of from about 0.1 mg/mL to about 250 mg/mL.

21. The composition of claim 1, wherein said surfactant is present in an amount of from about 10 mg/mL to about 150 mg/mL.

22. The composition of claim 1, wherein said surfactant is present in an amount of from about 20 mg/mL to about 100 mg/mL.

23. The composition of claim 1, wherein:
a) said spicamycin derivative is present in an amount of from about 2 mg/mL to about 4 mg/mL;
b) said first biocompatible alcohol is present in an amount of from about 250 mg/mL to about 350 mg/mL;
c) said glycerin or glycol is present in an amount of from about 600 mg/mL to about 700 mg/mL; and
d) said surfactant is present in an amount of from about 20 mg/mL to about 100 mg/mL.

24. The composition of claim 1, wherein:
a) said spicamycin derivative is present in an amount of from about 0.01 mg/mL to about 0.03 mg/mL;
b) said first biocompatible alcohol is present in an amount of from about 2 mg/mL to about 3 mg/mL;
c) said glycerin or glycol is present in an amount of from about 4 mg/mL to about 7 mg/mL; and
d) said surfactant is present in an amount of from about 0.2 mg/mL to about 0.5 mg/mL.

25. The composition of claim 1, further comprising a second analgesic or drug.

26. The composition of claim 25, wherein said second analgesic or drug is an anti-inflammatory drug.

27. The composition of claim 1, wherein said biocompatible alcohol is selected from the group consisting of:
a) ethanol; and
b) t-butanol.

28. The composition of claim 1, wherein said glycol is selected from the group consisting of:
a) propylene glycol;
b) polyethylene glycol; and
c) polypropylene glycol.

29. The composition of claim 1, wherein said surfactant is selected from the group consisting of:
a) polysorbate;
b) a poloxamer;
c) n-dodecyl-b-maltoside;
d) tocopheryl-polyethylene glycol succinate;
e) polyethylene glycol;
f) a polyoxyl;
g) Solutol;
h) Pluronics;
i) sodium dodecyl sulfate;
j) SPAN; and
k) octoxynol-9.

30. The composition of claim 1, wherein said composition comprises:
a) KRN5500 in an amount of about 4 mg/mL;
b) ethanol in an amount of about 293 mg/mL;
c) propylene glycol in an amount of about 618 mg/mL; and
d) polysorbate 80 in an amount of about 40 mg/mL.

31. A method for preparing the composition of claim 1, said method comprising:

a) contacting said spicamycin derivative of Formula II:

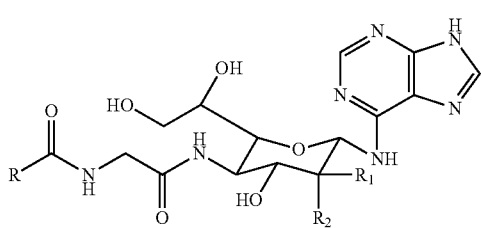

with a biocompatible alcohol that solubilizes said spicamycin derivative, and a surfactant soluble in said biocompatible alcohol, to form a first solution, wherein $R_1$ and $R_2$ are different from each other and represent H or OH, and R represents a substituted or unsubstituted alkyl, alkenyl, alkynyl, or cycloalkyl; and b) contacting said first solution with glycerin or a glycol that is miscible with said biocompatible alcohol to form said composition;
wherein said composition is substantially free of particulates, and wherein said composition is essentially free of monoethanolamine and wherein said composition is a single-phase solution.

32. The method of claim 31, further comprising the step of filtering said composition.

33. A method for preparing an intravenous solution, said method comprising contacting said composition of claim 1 with an intravenous infusion liquid or diluent to produce an intravenous solution, wherein said intravenous solution is substantially free of particulates.

34. A method for treating pain in a subject, said method comprising administering to a subject in need thereof a treatment or prevention effective amount of the composition of claim 1.

35. The method of claim 34, wherein said pain is neuropathic pain.

36. The method of claim 35, wherein said neuropathic pain is due to a neuropathy selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post-surgical pain syndrome, post mastectomy syndrome, post thoracotomy syndrome, phantom pain, nerve root avulsion, post radiation neuropathy, repetitive movement nerve injury, repetitive stress injury, and post injury neuropathy.

37. The method of claim 36, wherein said chemotherapy-induced neuropathy is selected from the group consisting of chemotherapy-induced peripheral neuropathy, painful chemotherapy-induced peripheral neuropathy, painful acute chemotherapy-induced peripheral neuropathy, and painful chronic chemotherapy-induced peripheral neuropathy.

38. The method of claim 34, wherein said composition is administered in a combination formulation comprising said composition and a second analgesic or drug.

39. The method of claim 38, wherein said second analgesic or drug is an anti-inflammatory drug.

\* \* \* \* \*

UNITED STATES PATENT AND TRADEMARK OFFICE
CERTIFICATE OF CORRECTION

PATENT NO. : 9,078,910 B2
APPLICATION NO. : 13/962279
DATED : July 14, 2015
INVENTOR(S) : Michael Radomsky, Mary Katherine Delmedico and Linda Jett It is certified that error appears in the above-identified patent and that said Letters Patent is hereby corrected as shown below:

IN THE CLAIMS:

Column 52, Line 19, "said first biocompatible" should read --said biocompatible--.

Column 52, Line 28, "said first biocompatible" should read --said biocompatible--.

Signed and Sealed this
Twenty-ninth Day of December, 2015

Michelle K. Lee
*Director of the United States Patent and Trademark Office*